United States Patent
Lynch et al.

(10) Patent No.: US 11,826,486 B2
(45) Date of Patent: *Nov. 28, 2023

(54) METHODS FOR TREATING WOUNDS

(71) Applicants: Samuel E. Lynch, Franklin, TN (US); Leslie Wisner-Lynch, Franklin, TN (US)

(72) Inventors: Samuel E. Lynch, Franklin, TN (US); Leslie Wisner-Lynch, Franklin, TN (US)

(*) Notice: Subject to any disclaimer, the term of this patent is extended or adjusted under 35 U.S.C. 154(b) by 296 days.

This patent is subject to a terminal disclaimer.

(21) Appl. No.: 17/122,890

(22) Filed: Dec. 15, 2020

(65) Prior Publication Data

US 2021/0121601 A1   Apr. 29, 2021

Related U.S. Application Data

(63) Continuation of application No. 16/045,520, filed on Jul. 25, 2018, now abandoned, which is a continuation of application No. 15/256,339, filed on Sep. 2, 2016, now Pat. No. 10,071,182, which is a continuation of application No. PCT/US2015/055522, filed on Oct. 14, 2015.

(60) Provisional application No. 62/063,793, filed on Oct. 14, 2014.

(51) Int. Cl.
| | |
|---|---|
| *A61K 38/18* | (2006.01) |
| *A61K 47/42* | (2017.01) |
| *A61K 9/70* | (2006.01) |
| *A61L 26/00* | (2006.01) |
| *A61K 9/00* | (2006.01) |
| *A61K 47/34* | (2017.01) |
| *A61P 17/02* | (2006.01) |

(52) U.S. Cl.
CPC ........ *A61L 26/0066* (2013.01); *A61K 9/0014* (2013.01); *A61K 9/0024* (2013.01); *A61K 9/7007* (2013.01); *A61K 38/1858* (2013.01); *A61K 47/34* (2013.01); *A61K 47/42* (2013.01); *A61L 26/0023* (2013.01); *A61L 26/0033* (2013.01); *A61L 26/0052* (2013.01); *A61L 26/0085* (2013.01); *A61L 26/0095* (2013.01); *A61P 17/02* (2018.01); *A61L 2300/414* (2013.01); *Y02A 50/30* (2018.01)

(58) Field of Classification Search
CPC ............. A61K 38/1858; A61K 9/0014; A61K 9/7007; A61L 26/0033; A61L 26/0023; A61L 26/0085; A61L 26/0095; A61P 17/02

See application file for complete search history.

(56) References Cited

FOREIGN PATENT DOCUMENTS

WO   WO-2009146456 A1 * 12/2009 ............. A61K 38/05

OTHER PUBLICATIONS

Reiber et al., Am J Surg. 1998; 176(Suppl 2A):5S-10S.*
Balfour et al., BioDrugs, 1999, vol. 11(5):359-364.*

* cited by examiner

*Primary Examiner* — Xiaozhen Xie

(57) ABSTRACT

Novel compositions for treating wounds and promoting the healing thereof are described, including composition containing novel combinations of a carrier and recombinant platelet derived grown factor having fewer isoforms and enhanced biostability. Methods of treating wounds with novel therapeutic composition using dosing procedures leading to effective results with a minimal number of treatment applications are also described.

74 Claims, 14 Drawing Sheets

Specification includes a Sequence Listing.

FIGS. 8A - 8D
FIG. 8A
Day 0
Control Collagen + Buffer wound dressing (weekly)
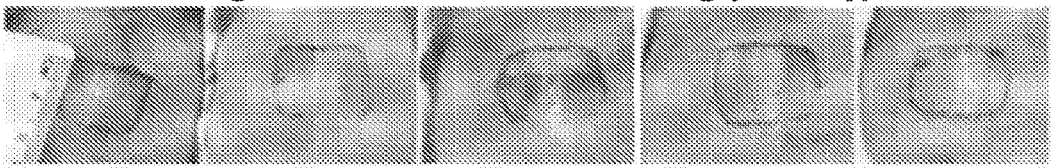
Collagen + pdgf dressing (weekly)
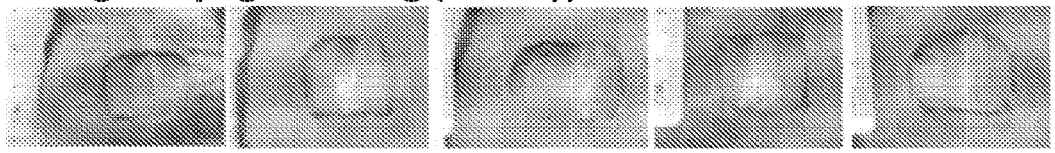
Regranex (daily)
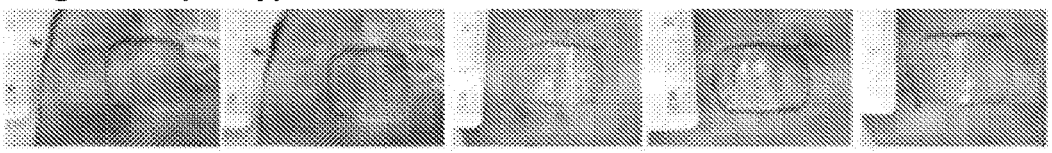

FIG. 8B        Day 7
Control Collagen + Buffer wound dressing (weekly)
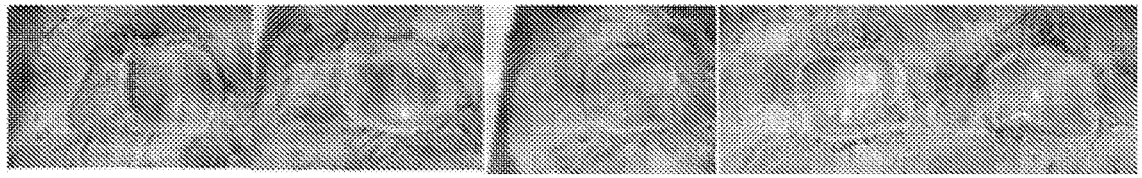
Collagen + pdgf dressing (weekly)
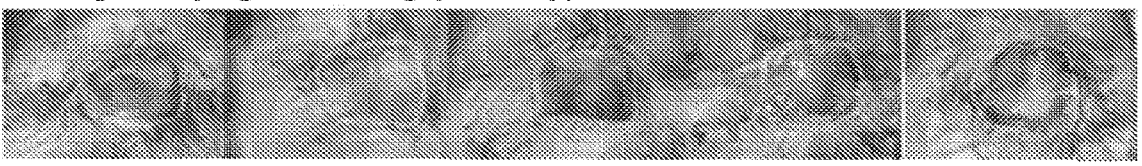
Regranex (daily)
Died 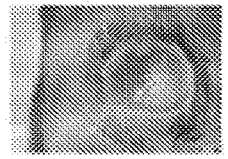 Died 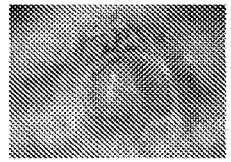 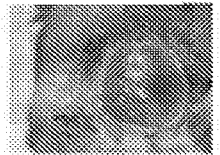
FIG. 8C        Day 14
Control Collagen + Buffer wound dressing (weekly)
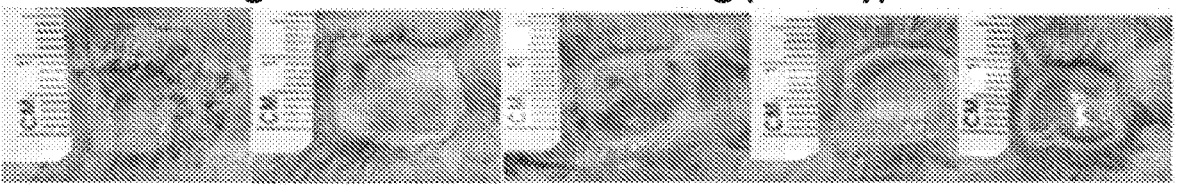
Collagen + pdgf dressing (weekly)
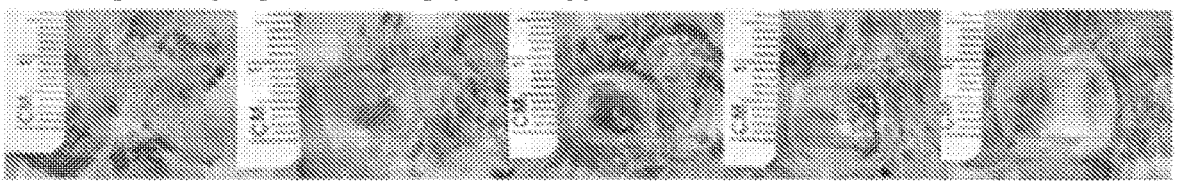
Regranex (daily)
Died 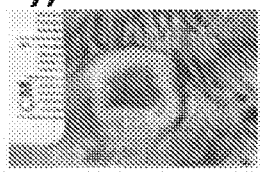 Died 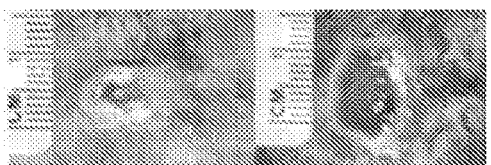

FIG. 8D    Day 21
Control Collagen + Buffer wound dressing (weekly)
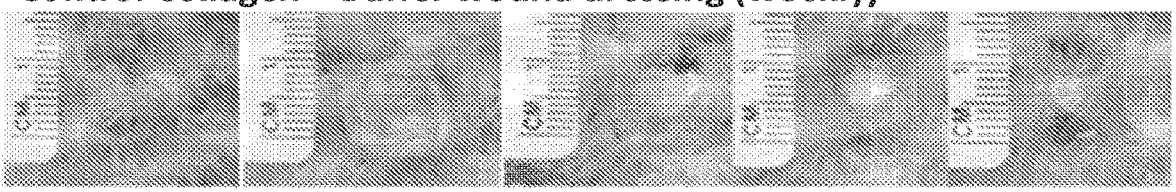
Collagen + pdgf dressing (weekly)
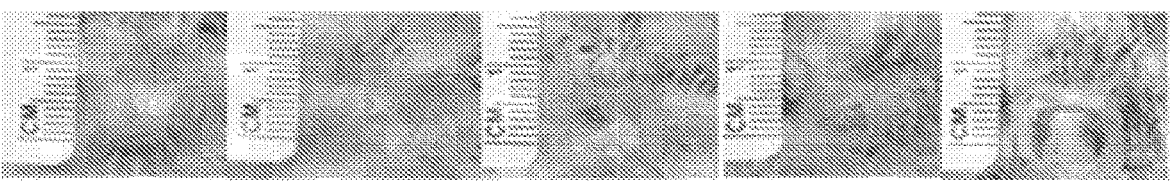
Regranex (daily)
Died    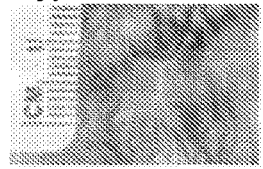    Died    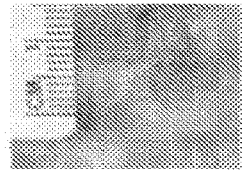    Died

METHODS FOR TREATING WOUNDS

CROSS REFERENCE TO RELATED APPLICATION

This application is a continuation of U.S. application Ser. No. 16/045,520, filed on Jul. 25, 2018, now abandoned, which is a continuation of U.S. application Ser. No. 15/256,339, filed on Sep. 2, 2016, now U.S. Pat. No. 10,071,182 issued on Sep. 11, 2018, which claims the benefit of PCT/US2015/055522, with an International Filing Date of Oct. 14, 2015, which claims the benefit of U.S. Provisional Application Ser. No. 62/063,793, filed Oct. 14, 2014, the entire contents of each application are incorporated herein by reference.

SEQUENCE LISTING

The instant application contains a Sequence Listing which has been submitted in ASCII format via EFS-Web and is hereby incorporated by reference in its entirety. Said ASCII copy, created on Jan. 22, 2019, is named 15256339.txt and is 2,000 bytes in size.

TECHNICAL FIELD OF THE INVENTION

The present invention relates to compositions and methods useful for treating wounds, and in particular, treating hard to heal wounds, such as lower extremity ulcers in a diabetic patient, venous stasis ulcers, pressure ulcers, severe burns and large surgical wounds such as abdominoplasties and other types of surgical tissue flaps.

BACKGROUND ART OF THE INVENTION

Diabetes is at epidemic proportions worldwide. Reportedly, around 370 million people have diabetes and this number is increasing in every country. One of the most common and serious complications resulting from diabetes is poorly healing wounds that develop most commonly on areas of high pressure on the surface of the foot, such as under the hallux (big toe), metatarsophalangeal joints, the tops and ends of the toes, the middle and sides of the foot and the heel. Foot ulcers form as a result of nerve damage resulting in a loss of sensation over such pressure points on the foot, which leads to extended microtrauma, breakdown of overlying tissue, and eventual ulceration. In addition, this loss in sensation can allow minor scrapes or cuts to go without proper treatment and eventually lead to the formation of ulcers. A significant percentage of diabetics will develop a foot ulcer during their lifetime. Once a diabetic foot ulcer (DFU) is formed, treatment can be challenging, particularly in view of the compromised healing environment due to the presence of neuropathy, vascular disease, altered neutrophil function, diminished tissue perfusion and/or defective protein synthesis, all of which often accompany diabetes.

There is a great need for better treatment modalities for these chronic ulcerations. DFUs are a leading cause of amputation. The longer these wounds remain, the greater the opportunity for them to increase in size and depth and become infected. As a consequence, these complications result in 80,000 amputations annually in the U.S. alone. This chronic pathology also severely compromises the overall health of the patient leading to a further downward health spiral of these patients, and additional costs to the health care system; their treatment doubles the cost of care for affected diabetic patients.

The principle aim of DFU management is wound closure. Under the current standard of care, DFU wound care focuses on radical and repeated debridement, frequent inspection and bacterial control, off-loading of any pressure on the wound, and careful moisture balance to prevent maceration. Effective DFU healing, however, has not been consistently achieved through this approach, and results can depend heavily on patient compliance. As a result, adjunctive treatments have been developed to address DFUs. Consensus reports for the management of diabetic foot ulcers recommend that for ulcers showing less than 50% healing at 4 weeks following good standard wound care, advanced therapeutics should be considered in order to speed wound healing and decrease complications. Such advanced treatments include negative pressure wound therapy, biological dressings, bioengineered skin equivalents, hyperbaric oxygen therapy, platelet rich plasma and growth factors.

However, only a small number of these advanced wound-care products have been shown to accelerate DFU healing in prospective, randomized registration trials, and even some of those results have been called into question by other studies. Among the products that have been studied in prospective, randomized registration trials are included becaplermin (Regranex®; Smith and Nephew), a topical gel containing recombinant human platelet-derived growth factor B chain homodimer (rhPDGF-BB), BioChaperone PDGF-BB (Adocia, Lyon, France), a topical spray that includes molecules that complex with PDGF, two living skin equivalents: a bi-layered skin substitute (Apligraf®; Organogenesis, Inc., Canton, MA) and a human fibroblast-derived dermal substitute (Dermagraft®; Shire, Plc., Dublin, Ireland), and vacuum-assisted wound closure (V.A.C.®; KCl, San Antonio, TX). Other treatment modalities that have less rigorous trial data include collagen, platelet-rich plasma, silver products, hyperbaric oxygen and electrical stimulation.

Despite some favorable results from prospective, randomized registration trials for certain advanced wound-care products, their overall benefits have been disappointing, as evidenced by the continuing high amputation rates. The following results were reported in a published meta-analysis of 35 randomized, controlled trials evaluating diabetic foot ulcer advanced therapies:

Platelet-rich plasma did not improve diabetic ulcer healing compared to good standard wound care.
Dermagraft® biological skin equivalent in pooled results from three studies showed non-significant improvement compared to standard care, with ulcer healing favoring Dermagraft (35% versus 24%).
Apligraf® biological skin equivalent bi-layer has been reported to improve healing over good standard wound care (55% versus 34%, p=0.001; 2 studies).
5, Regranex® rhPDGF-BB showed improvement in the percentage of ulcers healed compared to placebo or good standard wound care (58% versus 37%, p=0.04; 7 studies).
V.A.C.® negative pressure wound therapy improved healing more than good standard wound care (43% versus 29%, p<0.05; 1 study).
There was low or insufficient evidence for all studies related to enhanced time to ulcer healing.
In addition, in four studies the incidence of complete wound closure for Regranex was reported as 50% or less (48%, 50%, 44%, and 36%).

Such advanced therapies have not resulted in a consistently effective solution to treating DFUs. In view of their mixed clinical results along with their greater product cost compared to standard therapy, none of these advanced therapies have been widely adopted as a new standard of care for treating DFUs.

As noted above, one such advanced therapy is Regranex gel (becaplerman), which consists of rhPDGF-BB at a concentration of 100 µg/g in sodium carboxymethylcellulose gel. Specifically, Regranex is formulated as a multi-use, non-sterile, low bioburden, preserved, sodium carboxymethylcellulose-based (CMC) topical gel, and is indicated for daily application to improve the healing of chronic DFUs over several months. The Regranex package insert (label) states that it should be applied daily up for up to 140 daily applications over a 20 week period, and even longer if the physician deems it appropriate at a dose equal to about 0.006 mg/cm$^2$ (6.25 µg) of wound surface area.

Regranex remains the state-of-the-art growth factor therapy for healing of wounds, as evidenced by the fact that it is the only recombinant growth factor product to receive FDA approval for treatment of chronic wounds, even though it was FDA-approved over 15 years ago. Moreover, no one has successfully developed another formulation of Regranex (i.e. rhPDGF-BB) since its FDA approval. While clinical and non-clinical data support its clinical use, we believe Regranex has a number of limitations including: 1) the need for daily applications to the DFU by the patient, requiring daily wound dressing changes by the patient; 2) the low dosing prescribed in the FDA-approved Instructions for Use, about 0.006 mg (6 µg) per cm$^2$ of wound surface area; 3) often imprecise dosing due to the difficulty the patient experiences in visualizing and applying the gel from a tube (similar to a toothpaste tube) onto the wound which is often located on the bottom of the foot; 4) the need to keep the product refrigerated (about 2-8° C.); 5) lack of sterility of the Regranex gel; 6) the need for prolonged patient use—up to, and potentially exceeding, 140 daily applications over about a five month period; and 7) the use of the carboxymethylcellulose-based (CMC) topical gel which lacks the ability to provide a biological matrix for cellular ingrowth.

Furthermore, Regranex has been only modestly accepted by the medical community as an effective treatment for DFUs. Following the European Medicines Agency (EMA) review of data from four Regranex efficacy clinical trials, the EMA concluded that a 30 µg PDGF/g formulation was less effective than a 100 µg PDGF/g and there was little difference between the 100 µg PDGF/g formulation and a 300 µg PDGF/g formulation. The EMA further concluded that the 100 µg PDGF/g product formulation possessed only "modest" efficacy.

Perhaps as a result of the "modest" efficacy of Regranex, the effectiveness of the active ingredient in Regranex (i.e., rhPDGF-BB) in treating wounds has been called into question. Park S A, Raghunathan V K, Shah N M, Teixeira L, Motta M J, et al. (2014) *PDGF-BB Does Not Accelerate Healing in Diabetic Mice with Splinted Skin Wounds*, PLoS ONE 9(8): e104447. doi:10.1371/journal.pone.0104447, reported the results from a study using a controlled full thickness splinted excisional wound model in db/db mice (type 2 diabetic mouse model). Two splinted 8 mm dorsal full thickness wounds were made in db/db mice, and were topically treated once daily with either 3 µg PDGF-BB in 30 µl of 5% PEG-PBS vehicle or an equal volume of vehicle for 10 days. The study concluded that PDGF-BB, although bioactive in vitro, failed to accelerate wound healing in vivo in the db/db mice using the splinted wound model.

While experts in the field question the effectiveness of Regranex's active ingredient, rhPDGF-BB, Applicants believe that there are a number of reasons for Regranex's questionable efficacy. First, Regranex is delivered to the wound site by a gel carrier. This formulation allows the rhPDGF to be cleared from the site within minutes to hours. Second, while the gel carrier is biocompatible, we believe it provides no substrate for cell and vascular ingrowth and in fact may be inhibitory to cell growth and migration in the wound thereby potentially slowing the healing process and resulting in suboptimal healing. Third, Regranex is non-sterile, only stable when stored at 2-8 degrees C. (refrigerated) and must be applied daily often to hard to reach anatomical sites, all leading to poor patient compliance; Fourth, although the clinic data showed no difference between the 100 µg/g formulation and the 300 µg/g formulation, Applicants believe that the growth factor in Regranex is at too low of a concentration for optimal cell recruitment and proliferation. The Regranex dose per square centimeter of wound surface area is only 6 µg and Applicants believe that is too low for optimal cell recruitment and proliferation. Fifth and finally, despite its commercial use on patients for the past 15 years, the Applicants believe that the growth factor that is included in Regranex is not fully potent. The rhPDGF used in Regranex is recombinantly produced in a yeast expression system. When expressed in yeast, the protein is excreted as a fully folded homodimeric protein consisting of two antiparallel B chains held together by two interchain disulfide bonds. However, during fermentation, internal proteolysis (clipping between residues Arg32 and Thr33) and C-terminal truncation (Arg32 and Thr109) may occur. Internal proteolysis yields three potential forms of rhPDGF-BB: intact (both B chains are intact), single-clipped (one B chain is clipped), and double-clipped (both B chains are clipped). Clipping also creates new C-terminal sites for further C-terminal truncations and leads to a very complex mixture of isoforms. Applicants believe that the non-intact isoforms of rhPDGF-BB that are included in Regranex are far less effective in treating DFUs than the fully intact isoform.

rhPDGF-BB has also been used in orthopedic and periodontal indications, wherein the healing environments and the healing processes are very different from dermal wounds. Two such products include Augment Bone Graft and GEM21S, both of which include rhPDGF-BB as an active ingredient. GEM21S, consisting of rhPDGF-BB solution and a particulate synthetic bone substitute, was FDA-approved in 2005 and is indicated to improve bone healing in chronic periodontal defects. Augment Bone Graft also consists of rhPDGF-BB solution and a particulate synthetic bone substitute. Augment is FDA approved, based on a 434 patient pivotal clinical trial in the US and Canada, for improving bone fusion in foot and ankle fusion following a single implantation into the bone defect during surgery. However neither of these products is indicated for treating dermal wounds, such as DFU's, and both focus on using the product to promote bone growth and fusion, a very different cellular and physiologic process from skin wound healing, through a single intra-surgical application. Like Regranex, the GEM21S and Augment Bone Graft products must be stored refrigerated (about 2-8° C.) compromising user convenience and compliance.

In summary, poor patient outcomes leading to high amputation rates, and conflicting scientific analyses demonstrate that there remains a need for a more predictable, patient/user friendly and consistently effective method and therapeutic composition for promoting dermal wound healing, including treating DFU's and other types of hard to heal wounds.

DISCLOSURE OF THE INVENTION

The inventive embodiments provided in this Disclosure of the Invention are meant to be illustrative only and to provide an overview of selected embodiments disclosed herein. The Disclosure of the Invention, being illustrative and selective, does not limit the scope of any claim, does not provide the entire scope of inventive embodiments disclosed or contemplated herein, and should not be construed as limiting or constraining the scope of this disclosure or any claimed inventive embodiment.

The present invention provides methods and compositions for treating or promoting the healing of a wound, such as lower extremity ulcers in a diabetic patient, venous stasis ulcers, pressure ulcers, severe burns, traumatic injuries and large surgical wounds such as abdominoplasties and other types of surgical tissue flaps. In some embodiments, the wound may extend into the subcutaneous tissue or beyond, or the wound may be a diabetic foot ulcer.

Provided herein is an improved formulation of rhPDGF-BB that simultaneously includes a combination of the following improvements and benefits 1) a carrier that facilitates maintaining an effective PDGF dosage at a wound site for an extended period of time; 2) a carrier that provides a substrate for cell attachment and vascular ingrowth; 3) is sterile and therefore safer; 4) does not have to be refrigerated and is therefore safer and easier for patients to handle; 5) is applied less frequently than current therapies, preferably about once every other week, which facilitates better patient compliance and ease of use; 6) has rhPDGF present at a higher concentration than prior art formulations; and 7) contains a more pure and potent rhPDGF-BB formulation with fewer isoforms than certain prior art formulations. In certain embodiments of the invention, all of the above improvements and benefits are simultaneously realized.

Provided herein is a method of treating wounds comprising applying a therapeutic composition to the wound surface, monitoring the healing of the wound, and periodically reapplying the therapeutic composition to the wound surface, if deemed necessary, to achieve healing. In some embodiments, the method further includes debriding the wound to remove necrotic or infected tissue before applying the therapeutic composition and covering the wound with a dressing following the application of the therapeutic composition. In certain embodiments, a semi-occlusive or occlusive dressing, and the dressing may be periodically changed, such as changing the dressing with each reapplication of the therapeutic composition. The method of the present invention may also include the step of cleaning the wound at a dressing change with saline or an appropriate antiseptic wound cleansing agent and/or debriding chemical agent. The methods provided herein may also include treating the patient with a form of infection control or negative pressure wound therapy.

In some embodiments, the method further comprises forming the therapeutic composition by combining sterile PDGF and a sterile biocompatible matrix. The sterile PDGF may be a pre-formulated sterile PDGF solution or it may be formed as part of the treatment procedure by reconstituting a lyophilized sterile powder containing PDGF with a sterile water or buffer solution. In some embodiments, the biocompatible matrix is a sterile porous matrix and may be selected from the group consisting of natural polymers such as collagen, gelatin, fibrin, alginate, cellulose, or fibronectin. Alternatively the biocompatible matrix is a sterile porous matrix selected from the group of synthetic polymers such as poly(DL-lactide-co-glycolide) (PLGA), poly(DL-lactide) (PDLA), poly(L-lactide)(PLLA), poly(e-caprolactonePCL), polyurethane or others. In some embodiments, the biocompatible matrix is a collagen sponge or a mixture of natural and synthetic polymers.

In some embodiments the therapeutic composition is formed directly on the wound surface by either first applying a matrix, such as a collagen sponge, to the wound surface and then applying a PDGF solution to the collagen sponge, or alternatively by first applying a PDGF solution to the wound surface and then applying a matrix, such as a collagen sponge, to the wound surface. In some embodiments the therapeutic composition is formed by first forming a sterile PDGF solution by reconstituting a lyophilized sterile powder containing PDGF with a sterile water or buffer solution, and then aseptically adding the sterile PDGF solution to a sterile porous biocompatible matrix, such as a collagen sponge, in such a way that the matrix is wetted with the PDGF solution.

In accordance with another aspect of the present invention, there is provided herein a method of treating a dermal wound comprising: debriding the wound; applying a therapeutic composition containing recombinant platelet derived growth factor BB (rhPDGF-BB) to the wound about once every 3 to 42 days for a treatment period of about 2 to about 20 weeks, and wherein said first dose comprises at least about 10 µg of rhPDGF/cm$^2$ of wound surface area; and covering the wound with a dressing following each application of the therapeutic composition. In some embodiment, the method may further comprise advising said patient to avoid applying pressure on the wound as it heals. In some embodiments the cumulative total amount of rhPDGF-BB applied to the wound during the treatment period is less than about 25 mg or about 10 mg or about 5 mg or about 4 mg or about 3 mg or about 2 mg or about 1 mg of rhPDGF-BB. In some embodiments, the method comprises applying the therapeutic composition to the wound once every 7 to 28 days or once every 7 to 21 days or once every 10 to 15 days or once every 12 to 14 days. In some embodiments, each treatment includes application of at least about 10 µg of rhPDGF/cm$^2$ of wound surface area, or between about 10 µg of rhPDGF/cm$^2$ of wound surface area and about 5,000 µg of rhPDGF/cm$^2$ of wound surface area.

The present invention also provides a therapeutic composition comprising sterile PDGF and a biocompatible matrix that may be sterile and/or porous. In some embodiments, the sterile PDGF comprises a pre-formulated sterile PDGF solution, and in other embodiments the sterile PDGF comprises lyophilized sterile powder containing PDGF reconstituted with sterile water or buffer solution.

In certain embodiments, the sterile PDGF included in the therapeutic composition of the present invention comprises an rhPDGF-BB solution containing between about 0.05 mg/ml to about 5 mg/ml of rhPDGF-BB. The rhPDGF-BB solution may be formed by combining a sterile powder containing lyophilized rhPDGF-BB and sterile water or saline, thereby reconstituting the lyophilized rhPDGF-BB into solution. In certain embodiments, the rhPDGF-BB may be produced through an *E. coli* expression system wherein at least about 80% of said rhPDGF-BB on a weight basis is unclipped rhPDGF-BB, which may be subsequently lyophilized. In certain embodiments, the lyophilized rhPDGF-BB is capable of being stored at between about 20° C. and about 26° C. and still maintain the bioactivity of at least 80% of said rhPDGF-BB for at least about six months or at least about one year, or between about 16° C. and about 32° C. and still maintain the bioactivity of at least 80% of said rhPDGF-BB for at least about six months or at least about one year.

In certain embodiments, the matrix included in the therapeutic composition of the present invention may be selected from the group consisting of collagen, gelatin, fibrin, alginate, cellulose, Chitan or fibronectin. The matrix may provide a resorbable cell scaffold, and may comprise a collagen sponge. In certain embodiments, the matrix that has a pore size distribution of between about 10 microns to about 2,000 microns, and/or an average pore size of between about 50 microns to about 500 microns. In certain embodiments, some of the pores are interconnected or the majority of the pores are interconnected.

Also provided herein is a therapeutic composition comprising an rhPDGF-BB solution and a carrier, such as a matrix, wherein the ratio of the rhPDGF-BB solution to the matrix is between about 4 $\mu l/cm^3$ to about 40 $ml/cm^3$ or the ratio of rhPDGF-BB to the matrix is between about 1.2 µg PDGF/$cm^3$ of carrier to about 12 mg PDGF/$cm^3$ of carrier. The rhPDGF-BB solutions disclosed herein may comprise between about 0.05 mg/ml to about 5 mg/ml or between about 0.1 mg/ml to about 1 mg/ml or between about 0.2 mg/ml to about 0.4 mg/ml of rhPDGF-BB. The rhPDGF-BB solutions disclosed herein may comprise about 0.3 mg/ml or about 0.5 mg/ml or about 1.0 mg/ml of rhPDGF-BB. In certain embodiments, at least about 80% or about 85% or about 90% or about 95% or about 97% of the rhPDGF-BB included in the PDGF solution or the therapeutic composition on a weight basis is unclipped rhPDGF-BB.

In certain aspects, a therapeutic composition is provided comprising a rhPDGF-BB solution and a matrix wherein at least about 20% of the rhPDGF-BB is entrapped within the matrix' pores, such that when said composition is applied to a wound on a patient, the rhPDGF-BB is released over time as the matrix is absorbed by the patient's body. In certain embodiments, the therapeutic composition provides sustained delivery of rhPDGF-BB at the wound site as the matrix is resorbed and simultaneously provides a matrix for new cell and tissue ingrowth.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

BRIEF DESCRIPTION OF THE DRAWINGS

FIG. 7A graphically shows the amount of wound healing ($mm^2$) using ImageJ software per the number cumulative dosages for each of the four time point s (Day 0, Day 7, Day 14, and Day 21) for the Regranex Group 1 and rhPDGF/collagen Group 3. FIG. 7B shows the average percent healing for the Regranex Group 1, Collagen Group 2, and rhPDGF/collagen Group 3 at each of the four time points.

FIGS. 8, 8A-D graphically shows the average percent wound closure for each group over the treatment period: FIG. 8A shows Day 0; FIG. 8B shows Day 7; FIG. 8C shows Day 14; and FIG. 8D shows Day 21.

FIG. 9 illustrates the state of the wound in 15 test subjects on day 0 of the study.

FIG. 10 illustrates the state of the wound in 13 test subjects on day 7 of the study.

FIG. 11 illustrates the state of the wound in 13 test subjects on day 14 of the study.

FIG. 12 illustrates the state of the wound in 13 test subjects on day 21 of the study.

FIG. 13 is a photomicrograph (2× magnification) of a study control animal treated with a collagen sponge and buffer.

FIG. 14 is a photomicrograph (10× magnification) of a study control animal treated with a collagen sponge and buffer.

FIG. 15 is a photomicrograph (2× magnification) of a study animal treated with a composition in accordance with the present invention.

FIG. 16 is a photomicrograph (10× magnification) of a study animal treated with a composition in accordance with the present invention.

FIG. 17 is a photomicrograph (2× magnification) of a study animal treated with Regranex.

FIG. 18 is a photomicrograph (10× magnification) of a study control animal treated with Regranex.

MODES FOR CARRYING OUT THE INVENTION

Figure 1:
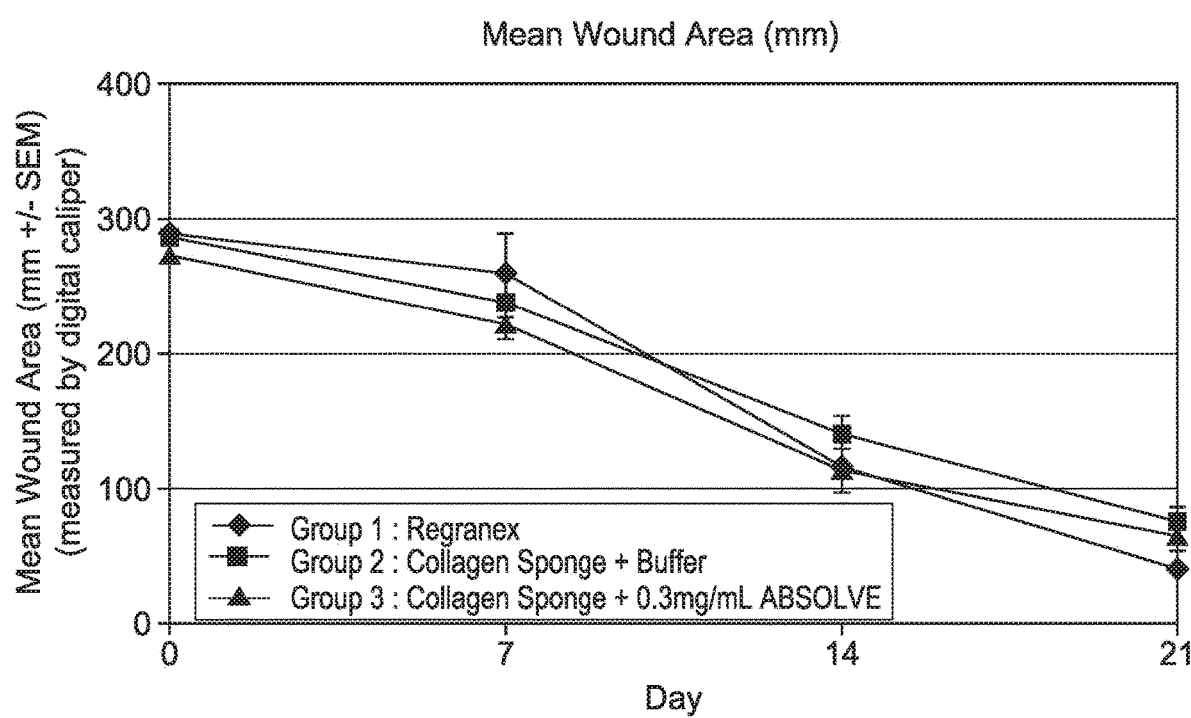
FIG. 1 graphically shows the changes in mean wound area over time in three groups of animals included in a study as calculated by digital caliper measurements.

The present invention provides for a novel method of treating dermal wounds, such as diabetic foot ulcers (DFUs), venous stasis ulcers, pressure ulcers, burns, tramatic injuries and large surgical wounds. The present invention additionally provides for novel bioactive therapeutic compositions for use in treating such wounds, novel methods of preparing bioactive dressings useful for the treatment of wounds, and novel treatment regimens to improve patient compliance and wound healing.

The novel methods and therapeutic compositions in accordance with the present invention will enable equivalent or superior efficacy compared to prior art products in treating dermal wounds, and provide a better safety profile and improved patient compliance and convenience. The novel therapeutic compositions provided herein provide: 1) prolonged delivery of the PDGF onto the wound from each application, thus obviating the need for far more frequent applications by the patient (e.g., daily or every other day applications with prior art products); 2) a physical material such as a collagen sponge that can be applied like a Band-Aid onto the wound once every several days thus improving patient compliance; 3) stability at room temperature, eliminating the need to keep the product refrigerated; 4) a sterile product improving safety over prior art products; 5) a higher initial dose of PDGF compared to prior art products which better initiates the healing process thus reducing the need for prolonged patient use; 6) the use of an improved carrier that not only sustains the delivery of the PDGF but simultaneously provides a biological scaffold and/or open porous matrix that facilitates ingrowth of cells, blood vessels and new tissue leading to improved healing compared to prior art products which lack the ability to provide a biological matrix for cellular ingrowth; and 7) contains a more pure and potent rhPDGF-BB formulation with fewer isoforms than prior art formulations. The novel methods disclosed herein provide: 1) a higher initial dose of PDGF as compared to prior art products to better initiate the healing process, thus reducing the need for prolonged patient use; and 2) a treatment protocol that will facilitate improved patient compliance and convenience by requiring fewer periodic applications of the therapeutic composition, perhaps as few as 1 to 6 applications versus the 140 applications required by prior art products.

I. Definitions/Nomenclature

As used herein unless otherwise indicated, open terms such as "contain," "containing," "include," "including," and the like mean comprising.

Some embodiments herein contemplate numerical ranges. When a numerical range is provided, the range includes the range endpoints unless otherwise indicated. Unless otherwise indicated, numerical ranges include all values and subranges therein as if explicitly written out.

Some values herein are modified by the term "about." In some instances, the term "about" in relation to a reference numerical value can include a range of values plus or minus 10% from that value. For example the amount "about 10" can include amounts from 9 to 11. In other embodiments, the term "about" in relation to a reference numerical value can include a range of values plus or minus 10%, 9%, 8%, 7%, 6%, 5%, 4%, 3%, 2%, or 1% from that value.

As used herein, the article "a" means one or more unless explicitly stated otherwise.

Where methods and steps described herein indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

The meaning of abbreviations is as follows: "C" means Celsius or degrees Celsius, as is clear from its usage, "µL" or "uL" or "U" means microliter(s), "mL" means milliliter(s), "L" means liter(s), "mm" means millimeter(s), "nm" means nanometers, "mM" means millimolar, "µM" or "uM" means micromolar, "M" means molar, "mmol" means millimole(s), "µmol" or "uMol" means micromole(s)", "g" means gram(s), "µg" or "ug" means microgram(s) and "ng" means nanogram(s), "% w/v" means weight/volume percent, "% v/v" means volume/volume percent, "HPLC" means high performance liquid chromatography, "UPLC" means ultra performance liquid chromatography, and "GC" means gas chromatography.

The term "homology" refers to the optimal alignment of sequences (either nucleotides or amino acids), which may be conducted by computerized implementations of algorithms. "Homology", with regard to polynucleotides, for example, may be determined by analysis with BLASTN version 2.0 using the default parameters. "Homology", with respect to polypeptides (i.e., amino acids), may be determined using a program, such as BLASTP version 2.2.2 with the default parameters, which aligns the polypeptide or fragments (and can also align nucleotide fragments) being compared and determines the extent of amino acid identity or similarity between them.

The above descriptions and methods for sequence homology are intended to be exemplary and it is recognized that this concept is well-understood in the art. Further, it is appreciated that nucleic acid sequences may be varied and still provide a functional enzyme, and such variations are within the scope of the present invention. The term "enzyme homolog" can also mean a functional variant.

As used herein, the term "carrier" is intended to refer broadly to any biologically compatible substance that can serve as a delivery vehicle for PDGF, whereas the terms "matrix" and "scaffold" are used interchangeable to refer to a carrier that acts as a substrate for cell attachment and/or vascular ingrowth as a wound heals, and/or provides a means for trapping the PDGF within its structure (such as, for example, through interconnected pores), thereby allowing for an ongoing or delayed or prolonged delivery of PDGF as a wound heals.

II. Novel Method of Treating Wounds

The present invention provides novel methods of treating of wounds. In one embodiment, a method of treating a wound comprises providing a therapeutic composition comprising a PDGF solution incorporated in a biocompatible scaffold, matrix or carrier and applying the therapeutic composition to a wound. A therapeutic composition comprising a PDGF solution incorporated in a biocompatible scaffold, matrix or carrier, for example, can be applied topically to the wound. In some embodiments, a method of treating a wound comprises multiple periodic applications of a therapeutic composition to a wound over a period of weeks.

In accordance with one aspect of the present invention, the novel treatment method for treating wounds includes the following steps:
 (1) debriding the wound as needed to remove necrotic or infected tissue;
 (2) forming a therapeutic composition comprising sterile rhPDGF-BB and a sterile porous biocompatible carrier;
 (3) applying the therapeutic composition containing PDGF to the wound surface, wherein the carrier provides a substrate for cell attachment and vascular ingrowth as the wound heals;
 (4) covering the wound with a dressing; and
 (5) monitoring the healing of the wound during a treatment period and repeating steps (1)-(4) at treatment intervals of 3 or more days.

The novel treatment method may further include preparing the novel therapeutic composition prior to applying it to the wound surface, wherein the composition comprises PDGF and a biological matrix. The method of preparing the composition may include:

(2a) reconstituting a lyophilized (freeze-dried) sterile PDGF powder with sterile water, saline, a buffer, or a physiologic solution to provide a specific safe and therapeutic concentration of PDGF; and (1b) withdrawing the sterile PDGF solution from a vial (container) and aseptically adding it to a dry hydrophilic sterile matrix or patch in such a way that the matrix or patch is wetted with the PDGF solution.

In some embodiments, the dressing is an occlusive or semi-occlusive dressing. In some embodiments, the repeat of steps (1)-(3) may also comprise the steps of: (A) removing the dressing and cleaning the wound with saline or an appropriate antiseptic wound cleansing agent prior to applying the therapeutic composition the dressing, and (B) covering the wound with a new dressing following application of the therapeutic composition. In some embodiments, novel bioactive therapeutic compositions described herein may be used in combination with other aspects of treating wounds, including for example infection control, negative pressure wound therapy, and/or instructing the patient to avoid placing pressure on the wound site.

In accordance with one aspect of the invention, there is provided a timing schedule for periodically retreating the wound, i.e. repeating steps (2)-(4) or periodically reapplying the therapeutic composition to the wound. The actual number of retreatments and the retreating frequency (i.e., the treatment interval) should be determined based on a number factors including the severity of the wound (e.g., its grade, size and depth), the extent to which the natural wound healing environment is compromised (e.g., the vascular supply at the site, the metabolic state of the patient, the ability to off-load pressure on the site, presence of infection, diabetes stage for a DFU, degree of burn for a burn), patient's age, duration of the wound, and other co-morbidities such as smoking, obesity, uncontrolled glucose levels, patient compliance and others. The number of retreatments and the retreatment frequency should be increased for more severe wounds or for wounds with more compromised healing environments. In addition, the prescribed number of treatments and/or the retreatment frequency may be adjusted during the treatment period based on the wound's rate of healing, i.e. increase number of retreatments and/or retreatment frequency for slower healing wounds, or decrease number of retreatments and/or retreatment frequency for faster healing wounds.

In accordance with one aspect of the invention, the retreatment frequency is at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, or at least about 15 days and so on up to at least about once every six weeks, or combinations thereof. In accordance with another aspect of the invention, the retreatment frequency is once every 2 to 42 days, or once every 3 to 42 days, or once every 2 to 28 days, or once every 3 to 28 days, or once every 2 to 7 days, or once every 3 to 7 days, or once every 4 to 21 days, once every 7 to 28 days, or once every 7 to 21 days, or once every 7 to 14 days, or once every 10 to 15 days, or once every 12 to 14 days. In accordance with another aspect of the invention, the retreatment frequency is once every 2 days, 3 days, 4 days, 5 days, 6 days, 7 days, 8 days, 9 days, 10 days, 12 days, 14 days, 15 days, 21 days, 28 days, 30 days, 35 days, 42 days, or combinations thereof.

In accordance with one another aspect of the invention, the retreatment frequency is substantially the same over the treatment period, and the retreatment frequency is one time at least about every 2 days, at least about every 3 days, at least about every 4 days, at least about every 5 days, at least about every 6 days, at least about every 7 days, at least about every 8 days, at least about 9 every days, at least about every 10 days, at least about every 11 days, at least about every 12 days, at least about every 13 days, at least about every 14 days, or at least about every 15 days and so on up to at least about once every six weeks.

In accordance with one aspect of the invention, the wound is retreated at least 1 time, at least 2 times, at least 3 times, at least 4 times, or at least 5 times over the treatment period. In accordance with another aspect of the invention, the wound is retreated between 0 and 6 times, between 0 and 7 times, or between 0 and 8 times over the treatment period. In accordance with another aspect of the invention, the wound is treated between 1 to 8 times, or between 2 to 7 times, or between 3 to 6 times over the treatment period. In accordance with another aspect of the invention, the wound is retreated 1, 2, 3, 4, 5, 6, 7, 8, 10, or 20 times over the treatment period. In accordance with another aspect of the invention the wound is retreated between 0 and 46 times, or between 1 and 46 times, or between 0 and 20 times, or between 1 and 20 times, or between 0 and 27 times, or between 1 and 27 times.

In accordance with one aspect of the invention, the cumulative total amount of rhPDGF-BB applied to the wound during the treatment period is preferably more than 0 mg, but less than about 50 mg, or less than about 25 mg, or less than about 20 mg, or less than about 15 mg, or less than about 10 mg, or less than about 5 mg, or less than about 4 mg, or less than about 3 mg, or less than about 2 mg, or less than about 1 mg of rhPDGF-BB. In certain embodiments, the cumulative total amount of rhPDGF-BB applied to the wound during the treatment period is preferably between about 0.1 mg to about 50 mg, or about 0.5 mg to about 25 mg, or about 1 mg to about 10 mg, or about 2.5 mg to about 8 mg, or about 3 mg to about 7 mg, about 4 mg to about 6 mg.

The various retreatments may involve the same or different dosages of rhPDGF-BB, either in terms of the exact amount of rhPDGF-BB that is applied to the wound (i.e., "absolute dosage") or in terms of the amount of rhPDGF-BB that is applied per square centimeter ($cm^2$) of wound area (i.e., "area dosage"). In accordance with one aspect of the invention, each treatment applies an absolute dosage of between about 10 µg and about 50 mg, or between about 10 µg and about 25 mg, or between about 10 µg and about 20 mg, or between about 10 µg and about 15 mg, or between about 10 µg and about 10 mg, or between about 10 µg and about 5 mg of rhPDGF-BB or between about 10 µg and about 1 mg or rhPDGF-BB. In accordance with another aspect of the invention, each treatment applies an area dosage between about 10 µg PDGF/$cm^2$ and about 1.0 mg PDGF/$cm^2$, or between about 10 µg PDGF/$cm^2$ and about 0.5 mg PDGF/$cm^2$, or between about 10 µg PDGF/$cm^2$ and about 0.25 mg PDGF/$cm^2$, or between about 10 µg PDGF/$cm^2$ and 0.1 mg PDGF/$cm^2$, or between about 10 µg PDGF/$cm^2$ and about 0.05 mg PDGF/$cm^2$. In certain embodiments, each treatment with rhPDGF-BB is preferably between about 10 µg to 1000 µg PDGF/$cm^2$, or about 0.01 mg to about 50 mg PDGF/$cm^2$, or about 0.05 mg to about 25 mg PDGF/cm², or about 0.1 mg to about 10 mg PDGF/cm², or about 0.2 mg to about 2 mg PDGF/cm². In certain embodiments, each treatment applies an area dosage that is at least about 10 µg of rhPDGF/cm² of wound surface area, or at least about 25 µg of rhPDGF/cm² of wound surface area, or at least about 50 µg of rhPDGF/cm² of wound surface area, or at least about 100 µg of rhPDGF/cm² of wound surface area, or at least about 250 µg of rhPDGF/cm² of wound surface area, or at least about 500 µg of rhPDGF/cm² of wound surface area. In certain embodiments, each treatment applies an area dosage that is between about 10 µg of rhPDGF/cm² of wound surface area and about 500 µg of rhPDGF/cm² of wound surface area, or between about 10 µg of rhPDGF/cm² of wound surface area and about 100 µg of rhPDGF/cm² of wound surface area, or between about 15 µg of rhPDGF/cm² of wound surface area and about 375 µg of rhPDGF/cm² of wound surface area, or between about 30 µg of rhPDGF/cm² of wound surface area and about 190 µg of rhPDGF/cm² of wound surface area, or between about 30 µg of rhPDGF/cm² of wound surface area and about 300 µg of rhPDGF/cm² of wound surface area.

In accordance with one aspect of the invention, the initial treatment with compositions in accordance with the present invention may be the most important treatment. PDGF facilitates the wound healing process through its effect on cell proliferation (mitogenesis) and directed cellular movement (chemotaxis) as well as re-vascularization (generating new blood vessels). Many cells have been shown to possess receptors (binding sites) for PDGF including connective tissue cells (skin, bone, cartilage, tendon and ligament), blood vessel cells and cells of the nervous system. Cells that possess receptors for PDGF respond by migrating toward the site of the wound (where PDGF is present at elevated levels as a result of applying therapeutic compositions in accordance with the present invention) and subsequently proliferating after binding PDGF. Since the PDGF receptor is degraded quickly after activation, cell proliferation is controlled and limited by the presence of locally available PDGF as well as by cell-cell interaction that leads cells to proceed from the proliferative phase of wound healing to that of matrix deposition that ultimately results in complete healing. As a result, a critical bolus of rhPDGF-BB must be applied during the initial treatment to ensure that the patient's natural wound healing process is properly activated. Therefore, in accordance with the invention the initial treatment comprises applying a therapeutic composition containing an area dosage that is at least 10 µg PDGF/cm² wound surface area, up to 5000 µg PDGF/cm² wound surface area, or at least 20 µg PDGF/cm² up to 1000 µg PDGF/cm² wound surface area, or at least 30 µg PDGF/cm² up to 600 µg PDGF/cm² wound surface area, or at least 40 µg PDGF/cm² up to 400 µg PDGF/cm² wound surface area, or at least 50 µg PDGF/cm² up to 350 µg PDGF/cm² wound surface area, or at least 60 µg PDGF/cm² up to 300 µg PDGF/cm² wound surface area, or at least 200 µg PDGF/cm² up to 2000 µg PDGF/cm² wound surface area. In accordance with another aspect of the invention the initial treatment comprises applying a therapeutic composition containing an area dosage that is at least 10 µg PDGF/cm² wound surface area, or at least 20 µg PDGF/cm² wound surface area, or at least 25 µg PDGF/cm² wound surface area, or at least 30 µg PDGF/cm² wound surface area, or at least 40 µg PDGF/cm wound surface area, or at least 50 µg PDGF/cm² wound surface area, or at least 60 µg PDGF/cm² wound surface area, or at least 70 µg PDGF/cm² wound surface area, or at least 80 µg PDGF/cm² wound surface area, or at least 90 µg PDGF/cm² wound surface area, or at least 100 µg PDGF/cm² wound surface area, or at least 250 µg PDGF/cm² wound surface area, or at least 500 µg PDGF/cm² wound surface area.

In accordance with another aspect of the invention, each treatment applies is between about 4 µl PDGF solution/cm³ of carrier (which may be a matrix such as a collagen sponge) to about 40 ml PDGF solution/cm³ of carrier, or between about 0.1 ml PDGF solution/cm³ of carrier to about 30 ml PDGF solution/cm³ of carrier, or between about 0.2 ml PDGF solution/cm³ of carrier to about 20 ml PDGF solution/cm³ of carrier, or between about 0.1 ml PDGF solution/cm³ of carrier to about 10 ml PDGF solution/cm³ of carrier, or between about 0.25 ml PDGF solution/cm³ of carrier to about 5 ml PDGF solution/cm³ of carrier, or between about 0.25 ml PDGF solution/cm³ of carrier to about 2.5 ml PDGF solution/cm³ of carrier, or between about 0.1 ml PDGF solution/cm³ of carrier to about 1 ml PDGF solution/cm³ of carrier, or between about 0.5 ml PDGF solution/cm³ of carrier to about 1.5 ml PDGF solution/cm³ of carrier. In certain embodiments, the PDGF solution contains about 0.3 mg/ml of rhPDGF-BB.

In accordance with another aspect of the invention, each treatment applies between about 1.2 µg PDGF/cm³ of carrier to about 12 mg PDGF/cm³ of carrier, or between about 30 µg PDGF/cm³ of carrier to about 9 mg PDGF/cm³ of carrier, or between about 60 µg PDGF/cm³ of carrier to about 6 mg PDGF/cm³ of carrier, or between about 75 µg PDGF/cm³ of carrier to about 3 mg PDGF/cm³ of carrier, or between about 75 µg PDGF/cm³ of carrier to about 1.5 mg PDGF/cm³ of carrier, or between about 75 µg PDGF/cm³ of carrier to about 750 µg PDGF/cm³ of carrier, or between about 120 µg PDGF/cm³ of carrier to about 600 µg PDGF/cm³ of carrier, or between about 150 µg PDGF/cm³ of carrier to about 450 µg PDGF/cm³ of carrier, or between about 75 µg PDGF/cm³ of carrier to about 225 µg PDGF/cm³ of carrier.

In accordance with one aspect of the invention, the initial PDGF treatment absolute dosage may be greater than the subsequent retreatment dosages. The initial PDGF treatment absolute dosage may be about 10%, about 20%, about 30%, about 40%, or about 50% higher, or up to about 300% higher than each of the subsequent retreatment PDGF dosages.

In accordance with one aspect of the invention, the method includes storing the PDGF at room temperature, generally between 16 and 32 degrees C. Prior to use it may be reconstituted with sterile water, saline, a buffer, or other physiologic solution to form a solution having the desired PDGF concentration. The solution is then added to a carrier, preferably a cell matrix (e.g., a collagen sponge) having the desired porosity in the desired volume to wet the matrix. The rhPDGF soaked matrix is then applied to the wound surface. If the wound is an external wound it is then covered with a wound dressing. This process may then be repeated in accordance with frequency and duration parameters described above until the wound is substantially healed.

III. Novel Therapeutic Compositions for Treating Wounds

The present invention also provides novel therapeutic compositions for treating wounds, which comprise sterile PDGF incorporated in a biocompatible sterile carrier, matrix or scaffold. For example, the therapeutic composition can be applied topically to a wound to facilitate the wound's healing.

In accordance with one aspect of the invention, a therapeutic composition is provided that comprises a rhPDGF-BB solution and a carrier that is preferably a biocompatible cell scaffold, wherein the rhPDGF-BB solution is disposed in or incorporated into the cell scaffold. In some embodiments, the rhPDGF-BB solution comprises between about 0.05 mg/ml to about 5 mg/ml of rhPDGF-BB, or between about 0.1 mg/ml to about 1 mg/ml of rhPDGF-BB, or between about 0.2 mg/ml to about 0.4 mg/ml of rhPDGF-BB. In accordance with one aspect of the invention, the rhPDGF-BB solution contains rhPDGF-BB at a concentration of about 0.05 mg/ml, or about 0.1 mg/ml, or about 0.2 mg/ml, or about 0.25 mg/ml, or about 0.3 mg/ml, or about 0.35 mg/ml, or about 0.4 mg/ml, or about 0.5 mg/ml, or about 0.6 mg/ml, or about 0.7 mg/ml, or about 0.8 mg/ml, or about 0.9 mg/ml, or about 1 mg/ml, or about 2 mg/ml, or about 3 mg/ml, or about 4 mg/ml, or about 5 mg/ml.

In some embodiments, the rhPDGF-BB solution is a preformulated aseptic PDGF solution comprising the elements described herein (e.g., PDGF concentration, sterile solution composition, etc.). In other embodiments the rhPDGF-BB solution is formed at the time of use, preferably by combining a sterile solution (e.g., sterile water, saline, a buffer solution, or a physiologic solution) with a sterile powder comprising or consisting essentially of lyophilized rhPDGF-BB. The sterile solution is used to reconstitute the lyophilized rhPDGF-BB. The lyophilized rhPDGF-BB is formed by lyophilizing liquid rhPDGF-BB produced by using a recombinant expression system as described further herein below under aseptic conditions.

In another aspect of the invention rhPDGF may be incorporated into carrier, preferably a sterile, biocompatible, absorbable cell scaffold, and the PDGF saturated carrier is then lyophilized to form a sterile, dry device incorporating rhPDGF. Any known technique for lyophilizing recombinant proteins may be used to lyophilize rhPDGF-BB so long as it yields a sterile powder. The resulting lyophilized rhPDGF-BB powder is capable of being stored at room temperature and still maintain at least about 80% of its bioactivity for at least about 6 months, or at least about 1 year, or at least about 2 years, or at least about 3 years. The sterile lyophilized device may then be applied directly to a wound site or wetted either by blood or other sterile solution prior to placement on the wound.

Because PDGF has a tendency to adhere to surfaces of a container, such as a vial, (particularly at higher pH's) achieving reconstitution of 100% of the lyophilized PDGF in a vial may be challenging. Therefore, in certain embodiments, additives may be included in the PDGF solution to lower its pH below about 7, or below about 6, or below about 5 or below about 4 or below about 3. Additives that may facilitate reconstituting the lyophilized PDGF include salts, carrier proteins such as albumin, or low pH solutions such as dilute acetic acid or hydrochloric acid. If the PDGF solution is too acidic, however, it could negatively impact the biocompatible scaffold. Therefore, in certain embodiments, the lyophilized PDGF is reconstituted in a solution having a pH below about 5, and once the PDGF is substantially fully reconstituted a base solution is added to increase the pH of the PDGF solution to between about 6 to about 8, or to increase it to about 7 before it is combined with the biocompatible scaffold. Such a pH adjustment step is particularly useful when the biocompatible scaffold is a collagen sponge.

The buffer solution used to reconstitute the lyophilized rhPDGF-BB may comprise, but is not limited to, water, saline, carbonates, phosphates (e.g. phosphate buffered saline), histidine, acetates (e.g. sodium acetate), acidic buffers such as acetic acid and HCl, and organic buffers such as lysine, Tris buffers (e.g. tris(hydroxymethyl)aminoethane), N-2-hydroxyethylpiperazine-N'-2-ethanesulfonic acid (HEPES), and 3-(N-morpholino) propanesulfonic acid (MOPS). Preferably, the buffer solution is sterile. Buffers can be selected based on biocompatibility with PDGF and the buffer's ability to impede undesirable protein modification. Buffers can additionally be selected based on compatibility with wound tissues. In one embodiment, sodium acetate buffer is used. The buffers can be employed at different molarities, for example, about 0.1 mM to about 100 mM, about 1 mM to about 50 mM, about 5 mM to about 40 mM, about 10 mM to about 30 mM, or about 15 mM to about 25 mM, or any molarity within these ranges. In some embodiments, an acetate buffer is employed at a molarity of about 20 mM.

As noted above, the rhPDGF-BB solution is combined with carrier to form a therapeutic composition. The carrier may be a matrix or scaffold that acts as a substrate for cell attachment and/or vascular ingrowth as a wound heals, and/or provides a means for trapping the PDGF within its structure (such as, for example, through interconnected pores), thereby allowing for an ongoing or delayed or prolonged delivery of PDGF as a wound heals and the matrix or scaffold is resorbed by the body. In some embodiments, the carrier or matrix is a biocompatible, resorbable cell scaffold. The carrier or matrix may comprise natural polymers such as collagen, gelatin, fibrin, alginate, cellulose, Chitosan or fibronectin. The carrier or matrix may also comprise synthetic biocompatible polymers selected from the group of synthetic polymers such as poly(DL-lactide-co-glycolide) (PLGA), poly(DL-lactide)(PDLA), poly(L-lactide)(PLLA), poly(e-caprolactone)(PCL), polyurethane or others. The carrier or matrix may also be a mixture of such natural and synthetic polymers. In some embodiments, the matrix comprises a collagen or gelatin sponge, which may be a Type 1 collagen sponge. A collagen sponge holds the rhPDGF at the wound site and concurrently provides a scaffold for cell growth, resulting in improved user friendliness and more rapid and complete healing. In one aspect the invention, the carrier or matrix, which may be a collagen sponge, has a porosity of between about 10 microns to about 2 mm, or about 50 microns to about 1000 microns, or about 100 microns to about 500 microns. The average pore size may be between about 50 microns to about 500 microns and wherein the majority of the pores are interconnected.

In some embodiments, carrier or matrix materials are bioresorbable. A carrier or matrix material, in one embodiment, can be at least 20%, 30%, 40%, 50%, 60%, 70%, 75%, 90% or 100% resorbed within one month subsequent to its application to the wound. Bioresorbability will be dependent on: (1) the nature of the material (i.e., its chemical makeup, physical structure and size); (2) the location within the body in which the material is placed; (3) the amount of material that is used; (4) the metabolic state of the patient (diabetic/non-diabetic, smoker, old age, etc.); and (5) the extent and/or type of wound treated.

In one aspect of the invention, the rhPDGF-BB solution and the carrier should be combined in an appropriate ratio in order to form a therapeutic composition that has optimal effectiveness in healing wounds. In some embodiments, the rhPDGF-BB solution and the carrier are combined at a ratio that is between about 4 μl PDGF solution/$cm^3$ of carrier (which may be a matrix such as a collagen sponge) to about 40 ml PDGF solution/$cm^3$ of carrier, or between about 0.1 ml PDGF solution/$cm^3$ of carrier to about 30 ml PDGF solution/$cm^3$ of carrier, or between about 0.2 ml PDGF solution/$cm^3$ of carrier to about 20 ml PDGF solution/$cm^3$ of carrier, or between about 0.1 ml PDGF solution/$cm^3$ of carrier to about 10 ml PDGF solution/cm³ of carrier, or between about 0.25 ml PDGF solution/cm³ of carrier to about 5 ml PDGF solution/cm³ of carrier, or between about 0.25 ml PDGF solution/cm³ of carrier to about 2.5 ml PDGF solution/cm³ of carrier, or between about 0.1 ml PDGF solution/cm³ of carrier to about 1 ml PDGF solution/cm³ of carrier, or between about 0.5 ml PDGF solution/cm³ of carrier to about 1.5 ml PDGF solution/cm³ of carrier.

In some embodiments, the rhPDGF-BB and the carrier are combined at a ratio that is between about 1.2 µg PDGF/cm³ of carrier to about 12 mg PDGF/cm³ of carrier, or between about 30 µg PDGF/cm³ of carrier to about 9 mg PDGF/cm³ of carrier, or between about 60 µg PDGF/cm³ of carrier to about 6 mg PDGF/cm³ of carrier, or between about 75 µg PDGF/cm³ of carrier to about 3 mg PDGF/cm³ of carrier, or between about 75 µg PDGF/cm³ of carrier to about 1.5 mg PDGF/cm³ of carrier, or between about 75 µg PDGF/cm³ of carrier to about 750 µg PDGF/cm³ of carrier, or between about 120 µg PDGF/cm³ of carrier to about 600 µg PDGF/cm³ of carrier, or between about 150 µg PDGF/cm³ of carrier to about 450 µg PDGF/cm³ of carrier, or between about 75 µg PDGF/cm³ of carrier to about 225 µg PDGF/cm³ of carrier.

In one aspect of the invention, the carrier is a scaffold and the rhPDGF-BB/scaffold ratio is such that when the rhPDGF-BB solution and the scaffold are combined, the scaffold is capable of entrapping at least about 20%, 30%, 40% or 50% up to at least about 100% of the rhPDGF-BB within the scaffold's pores such that the rhPDGF-BB is released over time as the scaffold is absorbed by the patient's body, thereby providing controlled delivery of rhPDGF-BB at the wound site over an extended period of time and simultaneously providing a matrix for new cell and tissue ingrowth. In some embodiments, the scaffold is capable of entrapping between about 20% to about 100%, or between about 25% to about 95%, or between 30% to about 90% of the rhPDGF-BB within the scaffold's pores. The percentages of PDGF entrapment described above are also applicable to entrapment of reconstituted lyophilized PDGF-BB.

Various amounts of rhPDGF-BB may be used in the therapeutic compositions of the present invention. In accordance with one aspect of the invention, the total amount of rhPDGF-BB included in the therapeutic composition is less than 50 mg, or less than 25 mg, or less than 10 mg, or less than 5 mg, or less than 2.5 mg or less than 1 mg. In accordance with another aspect of the invention the total amount of rhPDGF-BB included in the therapeutic composition is about 50 mg, or about 25 mg, or about 10 mg, or about 1.0 mg, or about 0.5 mg, or about 0.1 mg.

The concentration of PDGF in embodiments of the present invention can be determined by using an enzyme-linked immunoassay as described in U.S. Pat. Nos. 6,221,625, 5,747,273, and 5,290,708, incorporated herein by reference, or any other assay known in the art for determining PDGF concentration. The concentration of PDGF in the embodiments of the present invention is less than about 10 mg/g, or less than about 5 mg/g or less than about 1 mg/g or less than about 0.5 mg/g or less than about 0.1 mg/g or less than about 0.05 mg/ml. In another aspect of the invention the concentration of PDGF in the embodiments of the present invention is between about 0.05 mg/g to about 5 mg/g, or between about 0.1 mg/g to about 1 mg/g or between about 0.25 mg/g and about 0.5 mg/g.

The PDGF-BB used in the therapeutic composition of the present invention may be derived from any source such as natural source, synthetic source or recombinant source. In accordance with one aspect of the invention, PDGF is produced by recombinant DNA techniques. When PDGF is produced by recombinant DNA techniques, a DNA sequence encoding a single monomer (e.g., PDGF B-chain), is inserted into cultured cells for expression of the B chain monomer. The monomer is then extracted and isolated from the cell culture and refolded to form the biologically active homodimer (e.g., PDGF-BB), which may be further processed for additional purification. In accordance with one aspect of the invention, the cultured cells are prokaryotic cells or are *E. coli* cells. The rhPDGF-BB produced through these recombinant techniques can be purified in accordance with the techniques outlined in PCT No. WO 2005/077973, which is incorporated herein.

As noted above, prior art recombinant DNA production methods have resulted in mixtures of rhPDGF-BB fragments. In accordance with one aspect of the invention, substantially all of the rhPDGF-BB included in the therapeutic compositions described herein are intact non-clipped chains. In accordance with one aspect of the invention, the bacterial expression system is an *E. coli* expression system, and the resulting protein is purified using reversed phase high performance liquid chromatography, gel filtration or ion exchange chromatography, or some combination thereof, wherein the resulting rhPDGF-BB contained in the purified protein composition is at least about 80%, or at least about 85%, or at least about 90%, or at least about 95%, or at least about 97% unclipped rhPDGF-BB on a weight basis.

In some embodiments, the rhPDGF-BB included in the therapeutic compositions of the present invention is a rhPDGF-BB that comprises or consists essentially of an amino acid sequence having at least about 90%, about 92%, about 94%, about 96%, about 98%, about 99%, or about 100% homology to SEQ ID NO. 1, which is provided below:

```
                                                       SEQ ID NO. 1:
Ser Leu Gly Ser Leu Thr Ile Ala Glu Pro Ala Met Ile Ala Glu Cys Lys Thr Arg Thr
                5                  10                  15                  20

Glu Val Phe Glu Ile Ser Arg Arg Leu Ile Asp Arg Thr Asn Ala Asn Phe Leu Val Trp
                25                  30                  35                  40

Pro Pro Cys Val Glu Val Gln Arg Cys Ser Gly Cys Cys Asn Asn Arg Asn Val Gln Cys
                45                  50                  55                  60

Arg Pro Thr Gln Val Gln Leu Arg Pro Val Gln Val Arg Lys Ile Glu Ile Val Arg Lys
                65                  70                  75                  80

Lys Pro Ile Phe Lys Lys Ala Thr Val Thr Leu Glu Asp His Leu Ala Cys Lys Cys Glu
                85                  90                  95                  100

Thr Val Ala Ala Ala Arg Pro Val Thr
                105
```

In accordance with another aspect of the invention, the rhPDGF-BB included in the therapeutic compositions of the present invention comprises or consists essentially of at least about 80%, or at least about 85%, or at least about 90%, or at least about 95%, or at least about 97% unclipped rhPDGF-BB on a weight basis. In accordance with another aspect of the invention, the rhPDGF-BB included in the therapeutic compositions of the present invention comprises or consists essentially of at least about 80%, or at least about 85%, or at least about 90%, or at least about 95%, or at least about 97% of rhPDGF-BB that comprises or consists essentially of an amino acid sequence having at least about 90%, about 91%, about 92%, about 93%, about 94%, about 95%, about 96%, about 97%, about 98%, about 99%, or about 100% homology to SEQ ID NO. 1.

In some embodiments, the components comprising the novel compositions of the present invention are provided in a kit. A kit can comprise three components:
a) vial of sterile rhPDGF-BB lyophilized powder,
b) vial of sterile water, a buffer, saline, or a physiologic solution, and
c) a carrier.

The kit will may be stored at room temperature for up to 3 years. In some embodiments the storage is between 16 and 32 degrees C. In some embodiments, the powder included in the kit comprises a predetermined amount of PDGF. In some embodiments, the amount of PDGF is consistent with the values provided herein. In some embodiments, the carrier is included in a blister pack comprising a predetermined amount of carrier. In some embodiments, the amount of carrier is consistent with the values provided herein, and the type carrier is consistent with the materials described herein.

At the time of use, the rhPDGF-BB in the kit will be reconstituted with the sterile water, saline, buffer, or physiologic solution and the carrier will be shaped to the size of the wound. Following trimming the carrier to fit the wound, it will be soaked with the rhPDGF solution such that the solution fully saturates the interior pores of the carrier. The rhPDGF-saturated carrier will then be applied to the debrided wound and covered with a wound dressing. This process is repeated in accordance with the timing schedules described hereinabove.

IV. Methods of Treating Various Types of Wounds

The methods and compositions of the present invention are useful in treating a variety of wounds including diabetic ulcers, pressure ulcers, neuropathic ulcers, vascular ulcers, burns, accidental acute wounds and surgical wounds. Various wound classification systems exists and can be used to identify wounds that methods and compositions of the present invention are particularly useful in treating. Two such ulcer classification systems include the Wagner classification system (see, Wagner (1987) Orthopedics 10:163-72) and the University of Texas classification system (see, Lavery (1996) J Foot Ankle Surg 35:528-31). The Wagner system grades the wound by the depth of the wound and the presence of infection. It has five numeric grades:
Grade 1: Superficial Diabetic Ulcer
Grade 2: Ulcer extension
Involves ligament, tendon, joint capsule or fascia
No abscess or Osteomyelitis
Grade 3: Deep ulcer with abscess or Osteomyelitis
Grade 4: Gangrene to portion of forefoot
Grade 5: Extensive gangrene of foot
The University of Texas classification has four numeric grades based on the depth of the wound. In addition there are four letter grades, A to D, related to infection and ischemia.

The University of Texas classification system includes:
Stages
Stage A: No infection or ischemia
Stage B: Infection present
Stage C: Ischemia present
Stage D: Infection and ischemia present
Grading
Grade 0: Epithelialized wound
Grade 1: Superficial wound
Grade 2: Wound penetrates to tendon or capsule
Grade 3: Wound penetrates to bone or joint
A wound with a numeric grade of 3 and letter grade of D, for example, would be a wound that penetrates to bone or joint and is infected and ischemic. In accordance with one aspect of the present invention, the methods and compositions of the present invention are used to treat a wound that is either a grade 2, grade 3 or grade 4 wound under the Wagner classification system, or a grade 1, 2 or 3 wound (stages A, B, C, or D) under the University of Texas classification system.

In some embodiments, the methods and compositions described herein may be used to treat wounds such as lower extremity ulcers, and in particular foot ulcers on diabetic patients. The methods and compositions of the present invention are particularly useful in treating non-healing lower extremity diabetic ulcers which have failed to heal by about 50% after about 4 weeks of conventional therapies under the current standard of care as described above in the Background.

In some embodiments, the compositions of the present invention are used to treat burns in combination with a 1:1.5 or 1:1.3 meshed split thickness skin graft (the meshing allows the graft to cover a wider area but leaves small openings that need to heal), abdominoplasties (so-called "tummy tucks"), healing following other types of plastic and reconstructive surgeries, or post-amputation wounds.

V. Additional Therapeutic Elements

The therapeutic compositions of the present invention may include additional therapeutics elements to further facilitate healing a wound. In some embodiments, solutions comprising PDGF can further comprise additional components, such as other biologically active agents. In other embodiments, solutions comprising PDGF can further comprise cell culture media, other stabilizing proteins such as albumin, antibacterial agents, protease inhibitors [e.g., ethylenediaminetetraacetic acid (EDTA), ethylene glycol-bis (beta-aminoethylether)-N,N,N',N'-tetraacetic acid (EGTA), aprotinin, e-aminocaproic acid (EACA), etc.] and/or other growth factors such as fibroblast growth factors (FGFs), epidermal growth factors (EGFs), transforming growth factors (TGFs), keratinocyte growth factors (KGFs), insulin-like growth factors (IGFs), or other PDGFs including compositions of PDGF-AA, PDGF-BB, PDGF-AB, PDGF-CC and/or PDGF-DD. In addition, biologically active agents that can be incorporated into compositions of the present invention in addition to PDGF can comprise organic molecules, inorganic materials, proteins, peptides, nucleic acids (e.g., genes, gene fragments, small insert ribonucleic acids [si-RNAs], gene regulatory sequences, nuclear transcriptional factors, and antisense molecules), nucleoproteins, polysaccharides (e.g., heparin), glycoproteins, and lipoproteins. Additional non-limiting examples of biologically active compounds that can be incorporated into compositions of the present invention, including, e.g., anti-cancer agents, antibiotics, analgesics, anti-inflammatory agents, immunosuppressants, enzyme inhibitors, antihistamines, hormones, muscle relaxants, prostaglandins, trophic factors, growth factors, and vaccines, are disclosed in U.S. patent application Ser. No. 11/159,533 (Publication No: 20060084602).

Standard protocols and regimens for delivery of additional biologically active agents are known in the art. Additional biologically active agents can be introduced into compositions of the present invention in amounts that allow delivery of an appropriate dosage of the agent to the wound site. In most cases, dosages are determined using guidelines known to practitioners and applicable to the particular agent in question. The amount of an additional biologically active agent to be included in a composition of the present invention can depend on such variables as the type and extent of the condition, the overall health status of the particular patient, the formulation of the biologically active agent, release kinetics, and the bioresorbability of the biocompatible scaffold. Standard clinical trials may be used to optimize the dose and dosing frequency for any particular additional biologically active agent.

EXAMPLES

Example 1

The efficacy of a collagen wound dressing containing 0.3 mg/ml recombinant human platelet derived growth factor-BB (rhPDGF-BB) was evaluated in the treatment of surgically induced full thickness wounds in mice rendered diabetic by a mutation in the leptin receptor (db/db).

A. Study Design

Fifteen (15) male C57/B6 (Leprdb) db/db mice with an average starting body weight of 41.46 g were obtained from Jackson Laboratory (Bar Harbor, ME) strain code 000642. Animals were acclimatized prior to study commencement. During this period of 3 days, the animals were observed daily in order to reject animals that presented in poor condition.

During the study all animals were single housed under identical conditions in disposable cages. The study was performed in animal rooms provided with HEPA-filtered air at a temperature of 70° F.+/−5° F. and relative humidity of 50%+/−20%. Animal rooms were set to maintain a minimum of 12 to 15 air changes per hour. The room was on an automatic timer for a light/dark cycle of 12 hours on and 12 hours off with no twilight. AlphaDry® bedding was used. Bedding was changed a minimum of once per week. Cages, tops, bottles, etc. were washed with a commercial detergent and allowed to air dry. A commercial disinfectant was used to disinfect surfaces and materials introduced into the hood. Floors were swept daily and mopped a minimum of twice weekly with a commercial detergent. Walls and cage racks were sponged a minimum of once per month with a dilute bleach solution. A cage card or label with the appropriate information necessary to identify the study, dose, animal number and treatment group marked all cages. The temperature and relative humidity was recorded during the study, and the records retained. Animals were fed with a sterile Purina Labdiet® 5053 rodent diet and sterilized water was provided ad libitum.

At the commencement of the study, the fifteen (15) animals were randomly and prospectively divided into three (3) groups of five (5) animals each:

Group 1—Regranex Gel 0.01% rhPDGF-BB was applied daily for 21 days as prescribed by the package insert;

Group 2—a collagen wound dressing combined with buffer was applied on days 0, 7 and 14; and Group 3—a collagen wound dressing containing 0.3 mg/ml recombinant human platelet derived growth factor-BB (rhPDGF-BB) was applied on days 0, 7 and 14.

Each animal was identified by an ear punch corresponding to an individual number. On Day 0, mean starting weights were recorded, to ensure that mean starting weights were comparable among groups. A cage card was used to identify each cage or label marked with the study number (LYN-01), treatment group number, and animal numbers.

Test and control collagen+/−PDGF articles were administered topically as surgical dressings (as described below) immediately following the induction of the wound and were changed every seven (Q7) days. Regranex treated sites were treated as prescribed in the Instructions For Use (IFU) included in the product insert including daily dosing as outlined below. All dressings were applied and held in place using Tegaderm™ and secured in place outside of the wound area with benzoin. At the time of dressing change, the wound area was rinsed with saline and the rinse was collected and stored at −80° C. for future analysis of protease activity. For sites treated with the collagen wound dressing, all non-adherent collagen was gently removed from the healing wound, the site rinsed with saline and the rinse collected as described. Following removal of the dressing and collection of the rinse, the wound was measured using a caliper and photographed prior to re-application of dressing/test article. All wound areas were reported in $mm^2$.

For photographic documentation of wound healing, the camera was mounted on a tripod at an optimal distance to ensure all photos were consistent. A ruler was placed such that it was captured in the image to allow accurate estimation of lesion size. In addition to in life measurements of the wound area, all photographs of the wounds were analyzed using Image J Software and the wound area was traced and quantitated at the conclusion of the study.

Blood glucose levels were determined prior to the start of the study and again just prior to sacrifice on Day 21 to confirm diabetic disease state. At study termination, the wound site was collected in 10% NBF and prepared for histopathology. The study design is summarized below in Table 1.

TABLE 1

Study Design

| Group Number | Number of Animals | Wound (Day 0) | Treatment* | Route/ Frequency | Wound Assessment |
|---|---|---|---|---|---|
| 1 | 5 male (db/db) | 1.5 cm × 1.5 cm | Regranex Gel | Topical - 21 daily applications; dose applied based on open wound measurements at Day 0, 7 and 14** | Daily To Day 21 |
| 2 | 5 male (db/db) | 1.5 cm × 1.5 cm | Collagen wound dressing + Buffer | Topical - 3 weekly applications; Days 0, 7 and 14*** | Every 7 Days To Day 21 |
| 3 | 5 male (db/db) | 1.5 cm × 1.5 cm | PDGF Bioactive Wound Dressing | Topical - 3 weekly applications; Days 0, 7 and 14*** | Every 7 Days To Day 21 |

*All dressings were applied and held in place by Tegaderm ™
**The cm length of Regranex applied was based on open wound measurements obtained on Days 0, 7 and 14. The centimeter length of Regranex applied daily was the same for Days 0-6 and was based on measurements obtained on Day 0. The centimeter length of Regranex applied daily for Days 7-13 was based on measurements obtained on Day 7 and the centimeter length of Regranex applied on Days 14-21 was based on measurements obtained on Day 14. See "PDGF-BB Calculations" for detail.
***The volume of PDGF-BB or buffer/sterile saline that was applied to the collagen sponge at Days 0, 7 and 14 utilized the formula: 145 × $cm^2$ open wound surface area (length [cm] × width [cm] open wound)

B. Test Articles & Vehicle Preparation

The topical formulations used in the study were Regranex Gel (0.01% rhPDGF-BB in carboxymethylcellulose gel) (Group 1); acollagen wound dressing wetted with rhPDGF-BB (Group 3); and acollagen wound dressing wetted with saline (Group 2). All dressings were covered with Tegaderm™ and secured with benzoin.

1. Dressing Compositions a. Group 1 rhPDGF Dosage

As described in Regranex Package Insert, "each square centimeter of ulcer surface area will require approximately 0.25 cm length of gel squeezed from 15 gram tube". Formula: $(l \times w) \div 4 =$ cm length Regranex. For a 1.5 cm×1.5 cm square wound: $(1.5 \times 1.5) \div 4 = 0.56$ cm length Regranex. As described in Regranex Package Insert, "the weight of Regranex gel from 15 g tube is 0.25 g/cm length". Regranex is 0.01% rhPDGF-BB or 100 µg/g Regranex. For 0.56 cm length of product, the weight of product is 0.14 g for a total dose of PDGF-BB of 14 µg. For sites treated with Regranex for 21 days the maximum total dose for the study period (assuming no change in open wound size from Day 0) would be 14 µg/day×21 days or 294 µg of PDGF-BB. However, at Days 7 and 14 the open wound size was determined for all Regranex treated sites and the amount of Regranex applied was recalculated using the formula above ($[l \times w] \div 4 =$ cm length Regranex).

b. Group 3 rhPDGF and Group 2 Saline Dosages

The concentration of rhPDGF-BB used in the study was 0.3 mg/ml or 300 µg/ml. To not exceed a total dose for the study period of 294 µg PDGF-BB (same total maximum study dose as Regranex), a total of 0.98 ml of 0.3 mg/ml PDGF-BB would be applied to the wound site over the 21-day study period. Assuming a total of 3 administrations (days 0, 7 and 14), each administration would consist of ≈327 µl PDGF-BB onto the collagen sponge representing a dose of approximately 98 µg PDGFBB/administration (slightly more than 7× the initial individual dose for Regranex treated sites). This represents a total of 145 µl per square centimeter of open wound surface area (327 µl/2.25 $cm^2$ wound surface area).

The volume of 0.3 mg/ml PDGF-BB (Group 3) or buffer/sterile saline (Group 2) to be applied to the new collagen sponge on Days 7 and 14 was determined using the following formula:

145×$cm^2$ open wound surface area (length [cm]× width [cm] of open wound).

C. Collagen Sponge

As described above for Group 1 treated sites, all wounds were evaluated and measured at Days 7 and 14 to record the open wound measurements for each individual site. For sites treated with a collagen sponge (Group 2 and Group 3), the sponge was measured and trimmed to fit the open wound portion of the original wound following removal of the dressing, gentle rinsing of the site and documentation of findings including measurements and photographic documentation.

C. Surgical Procedures

On Day 0, animals were anesthetized with isoflurane. The hair on the back was clipped and the skin swabbed with an aseptic solution. A template was used to mark a 1.5×1.5 cm square on the mid-back of the animal and a full thickness wound, corresponding to the template, was made by excising the skin and the panniculus carnosus. A hot water circulation pad or equivalent was placed under the animal to maintain normal body temperature during procedures, and animals recovered on a similar hot water circulation pad. Buprenorphine (0.06 mg/kg) was given by subcutaneous injections immediately after recovery from anesthesia and every 12 hours thereafter for 72 hours. Warmed Ringers solution (0.5 mL) was given by sub-cutaneous injection after the mice have recovered consciousness. The wounding of the animal was carried out under aseptic conditions. The wound site was photographed and the length and width measured immediately after excision and daily thereafter using a digital caliper. From Days 0 to 21, mice were administered test articles as listed in Table 1.

D. Study Results

1. Animal Survival

Three animals died or were prematurely euthanized during this study (all animals from Group 1—Regranex). The first animal was found dead one day after surgery (Animal #3). The second animal (Animal #1) had to be sacrificed on Day 5 due to self-mutilating the rear flank posterior to the wound site. Animal #5 in Group 1 had to be sacrificed on day 16 as a result of losing more than 20% of its starting body weight. The following Table 2 summarizes the animal deaths/sacrifice:

TABLE 2

| Summary of Animal Deaths/Sacrifice | | |
|---|---|---|
| Day 1 | Day 6 | Day 16 |
| Group 1, Animal #3 Found Dead | Group 1, Animal #1 Sacrificed, Self Mutilating | Group 1, Animal #5 Exceeded 20% Weight Loss |

2. Wound Measurements

The wound area was measured using a digital caliper and the length (L) and width (W) of each wound was recorded. Wound area was calculated using the formula to calculate the area of a square where A=L×W. FIG. 1 shows the area of the wounds for each group on Days 0, 7, 14 and 21. Peak wound area was recorded on Day 0 for all three groups with subsequent decreases in mean wound area on Day 7, Day 14, and Day 21. All treated groups showed a substantial decrease in wound area during the course of the study.

Figure 2:
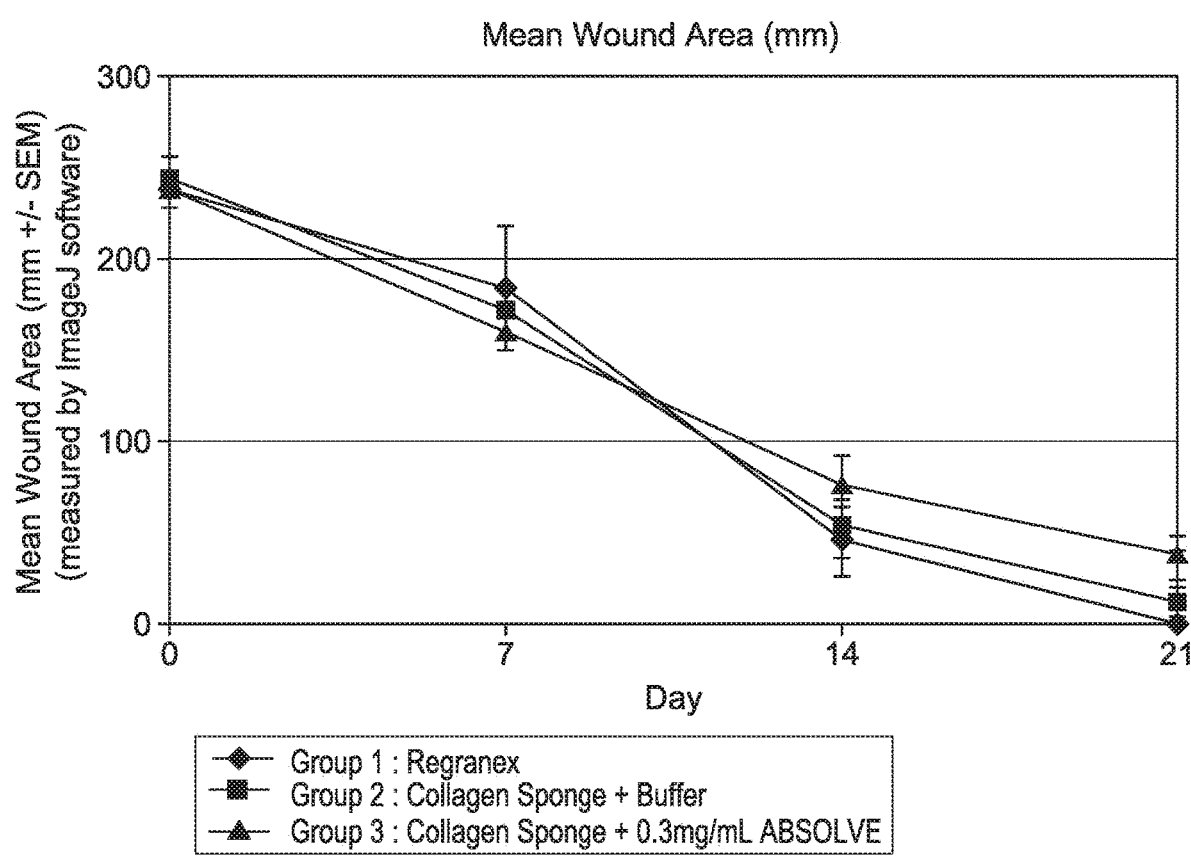
FIG. 2 graphically shows the changes in mean wound area over time in three groups of animals included in a study as calculated using ImageJ software.
Figure 3:
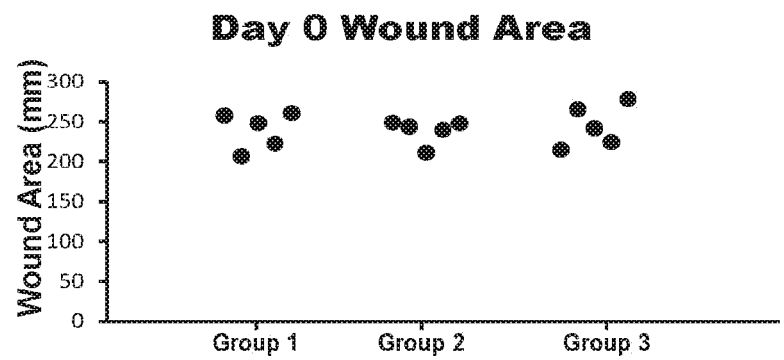
FIG. 3 graphically shows the wound area as calculated using ImageJ software for each test animal on day 0 of a study.
Figure 4:
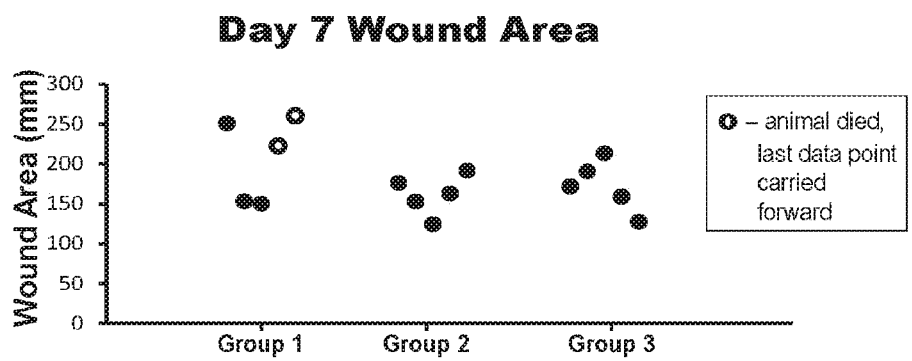
FIG. 4 graphically shows the wound area as calculated using ImageJ software for each test animal on day 7 of a study.
Figure 5:
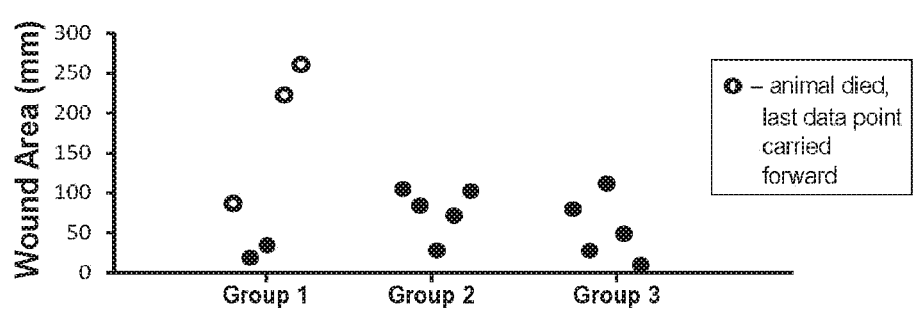
FIG. 5 graphically shows the wound area as calculated using ImageJ software for each test animal on day 14 of a study.
Figure 6:
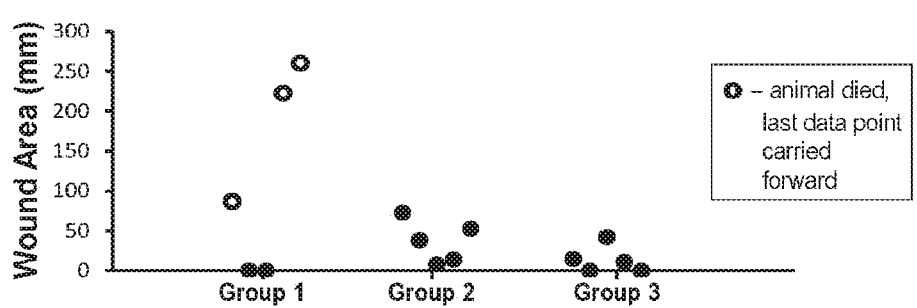
FIG. 6 graphically shows the wound area as calculated using ImageJ software for each test animal on day 21 of a study.
Figure 7:
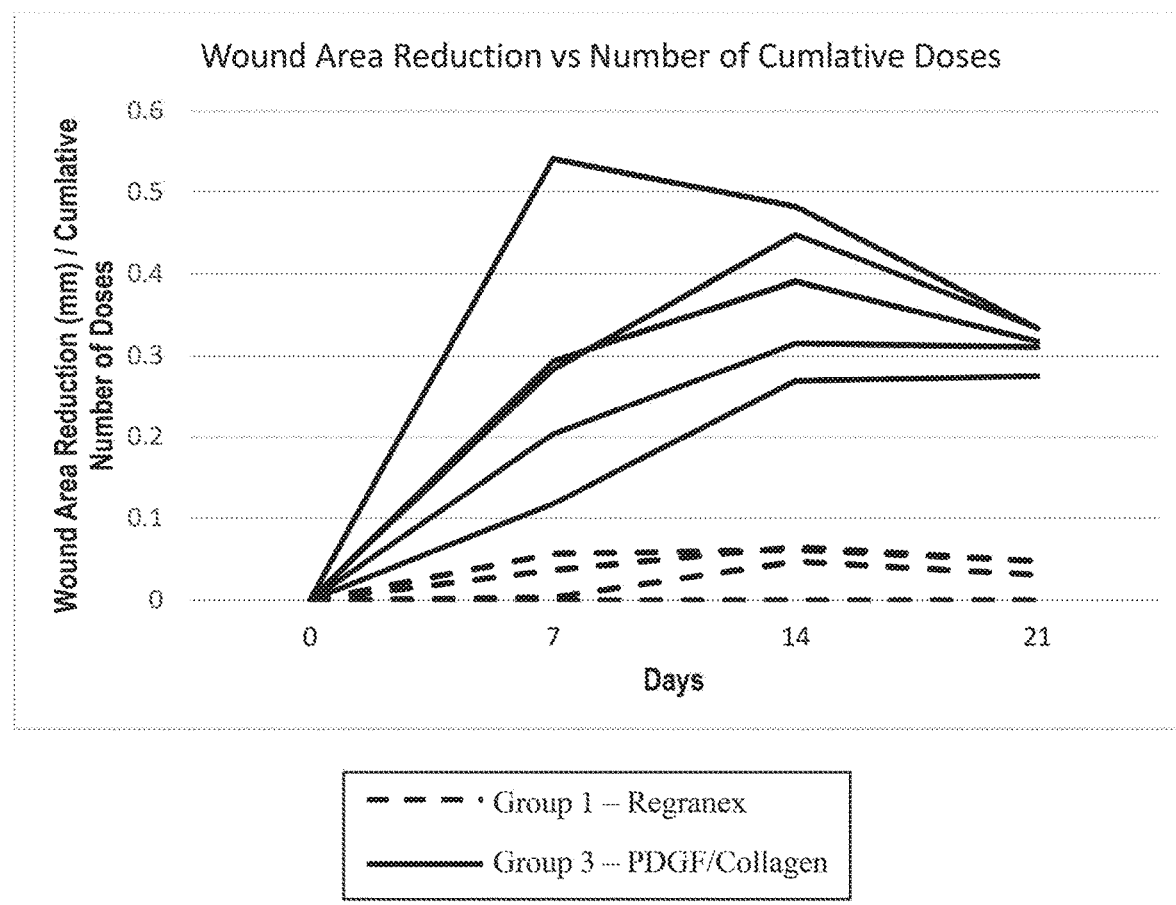
FIGS. 7, 7A-7B graphically show that positive results are achieved with fewer applications of the therapeutic composition.
Figure 7A:
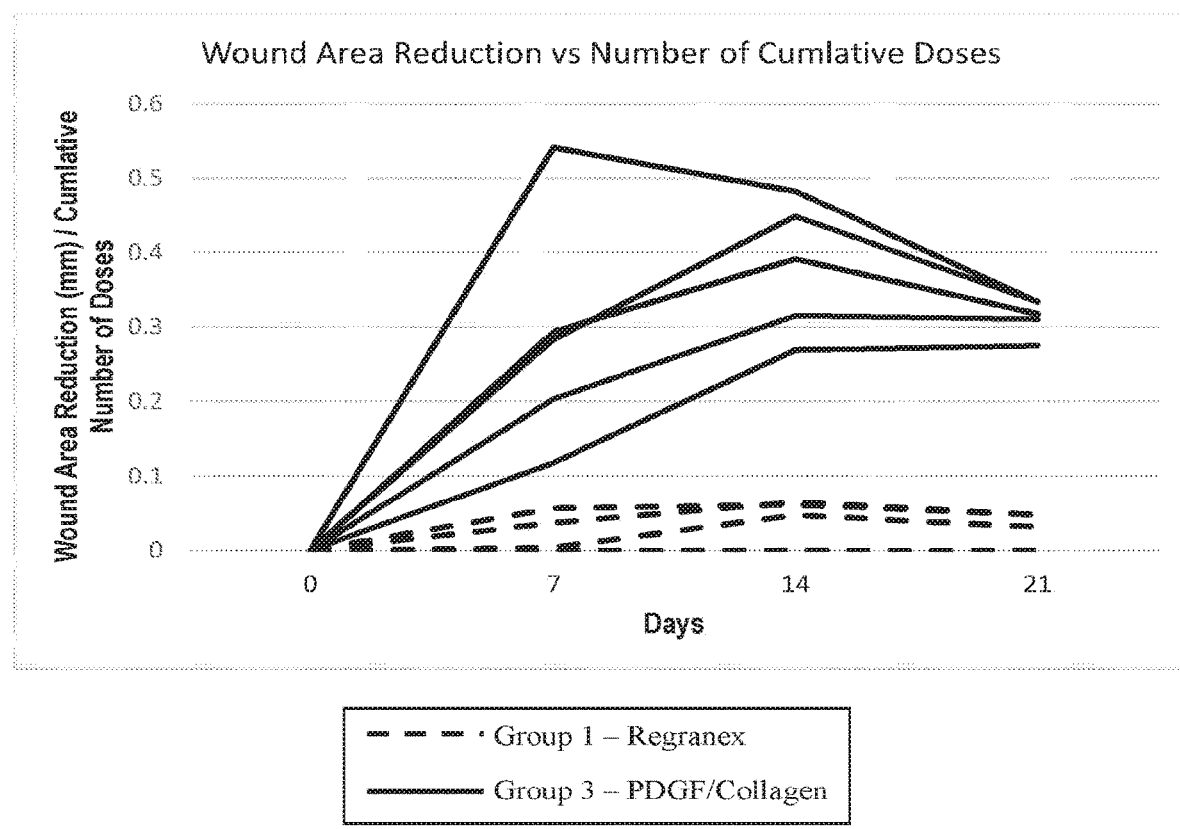
Figure 7B:
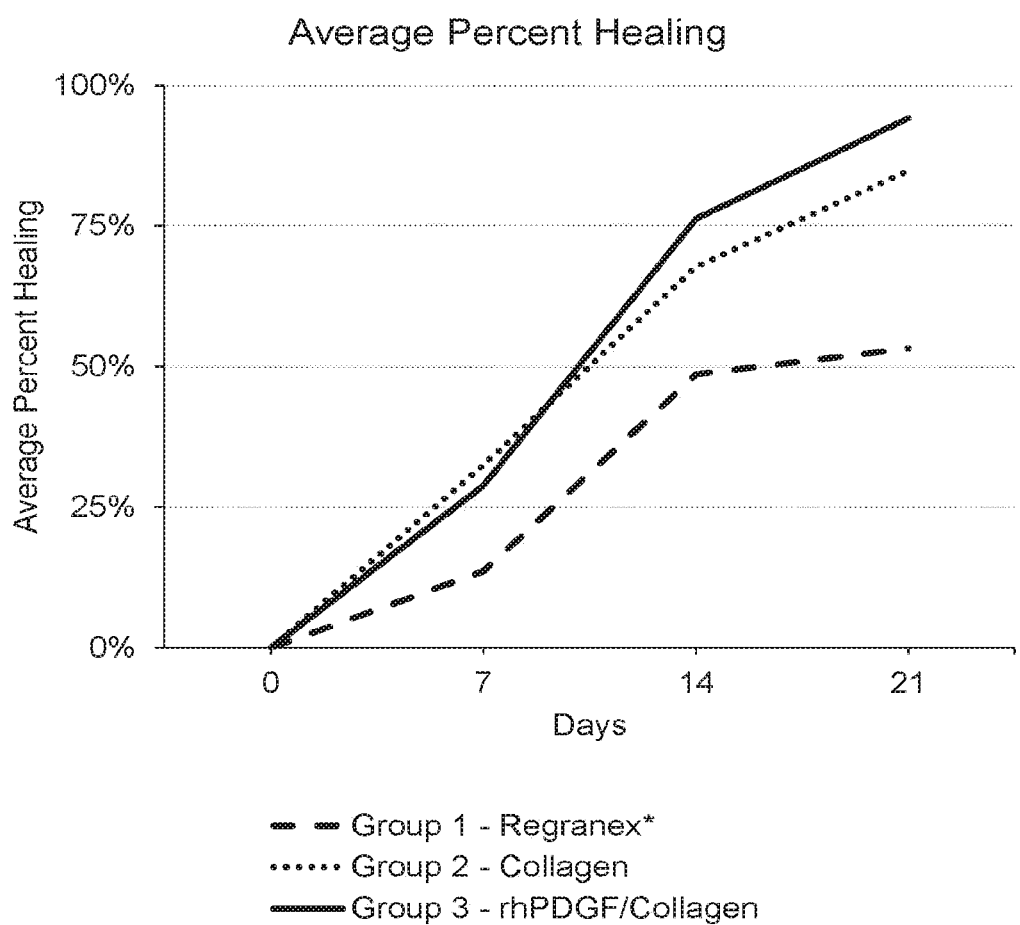
Figure 8:
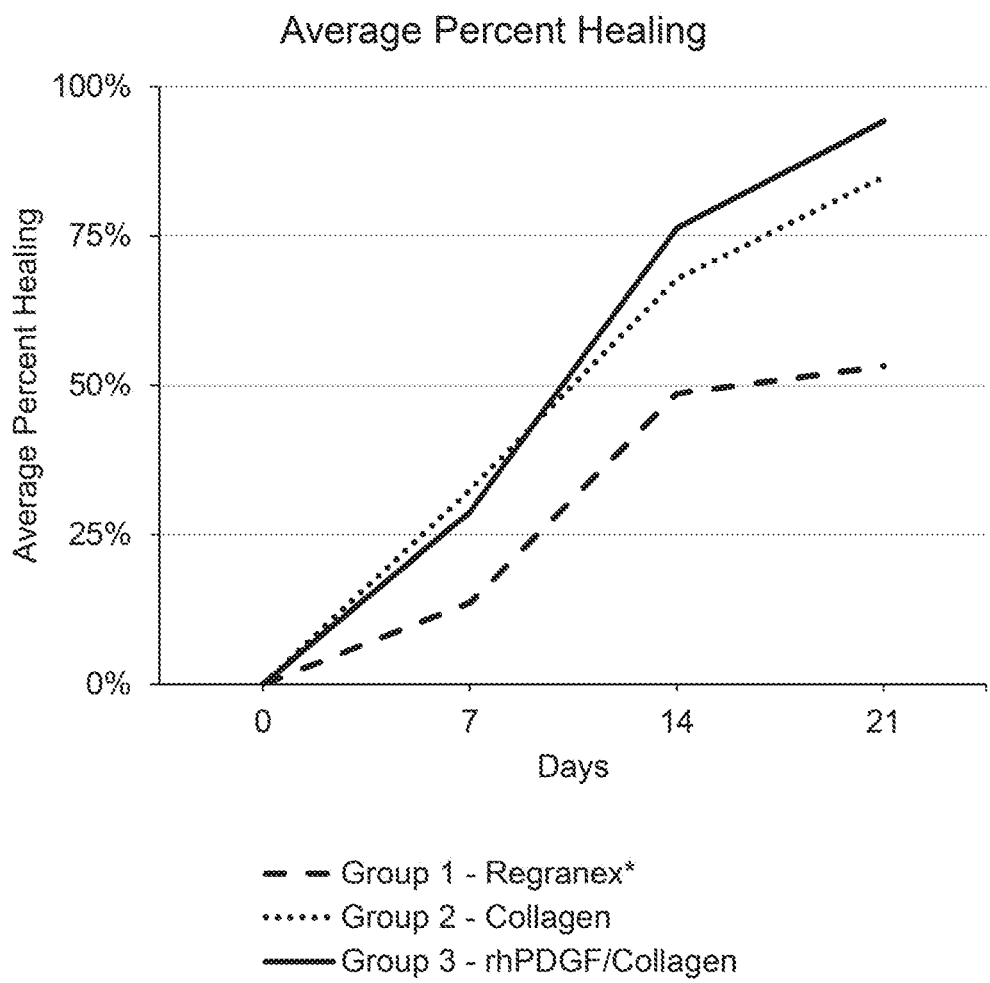
Figure 9:
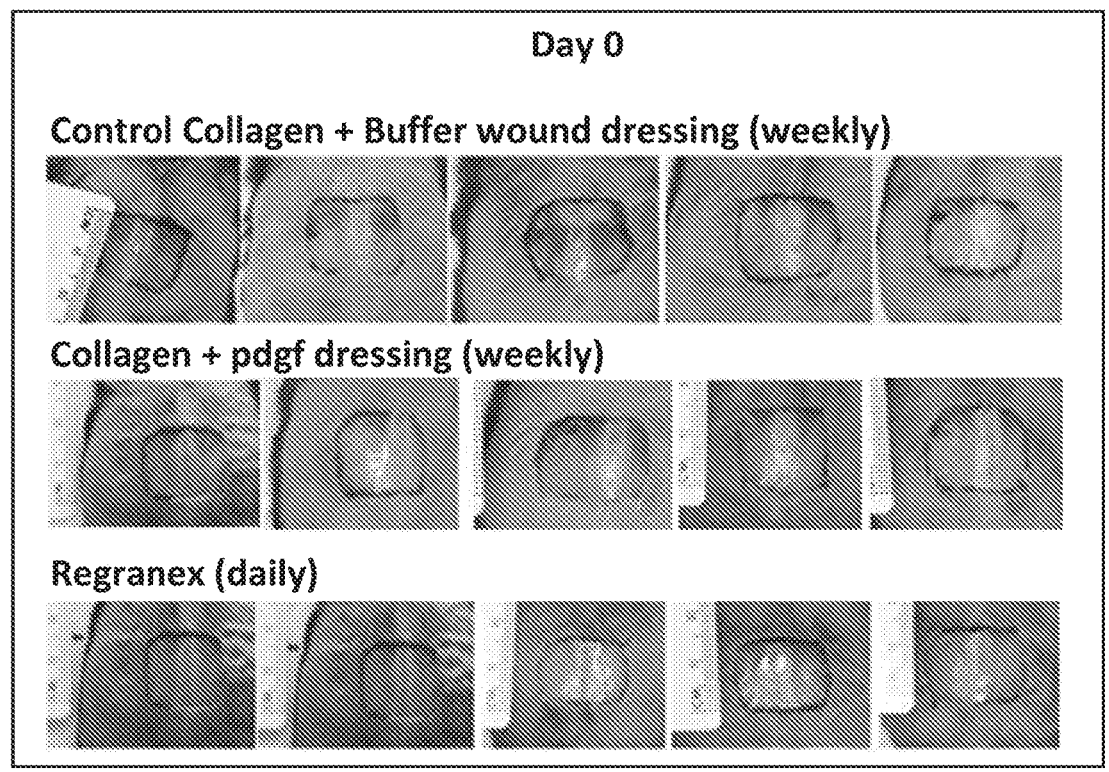
FIGS. 9-12 include a series of wound images showing the degree of healing over time for animals included in a study testing compositions in accordance with the invention.
Figure 10:
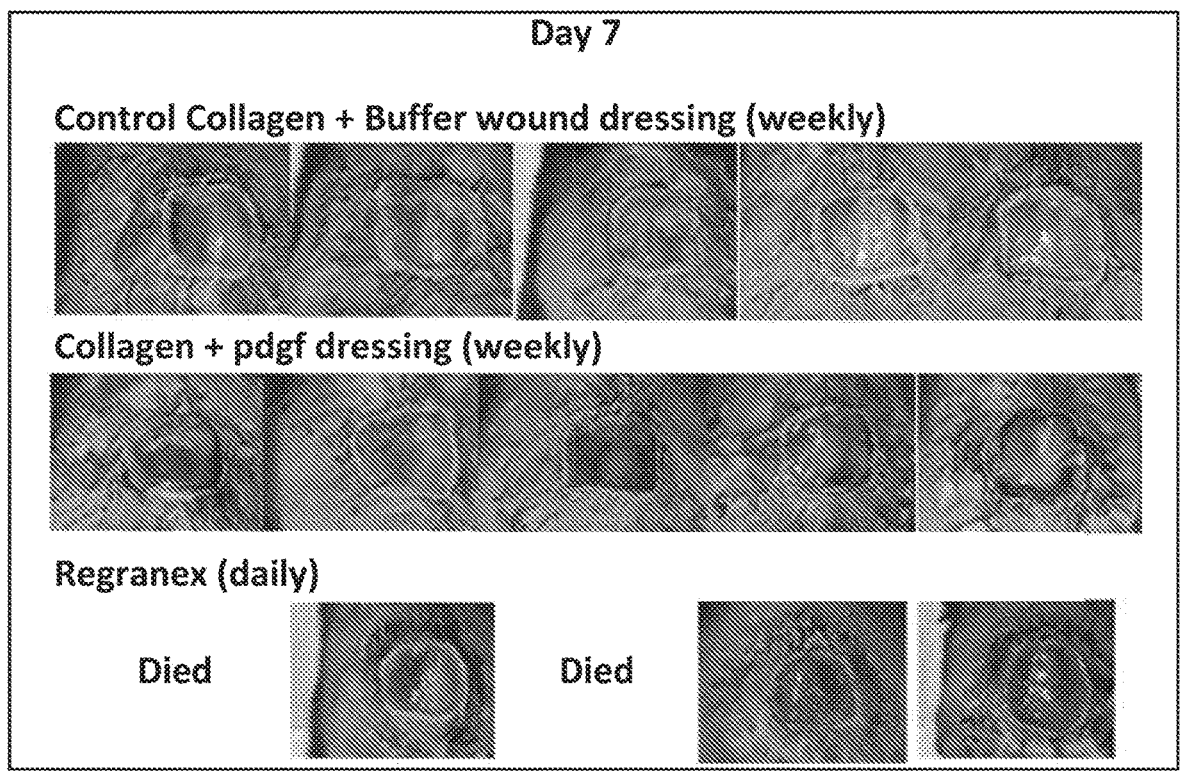
Figure 11:
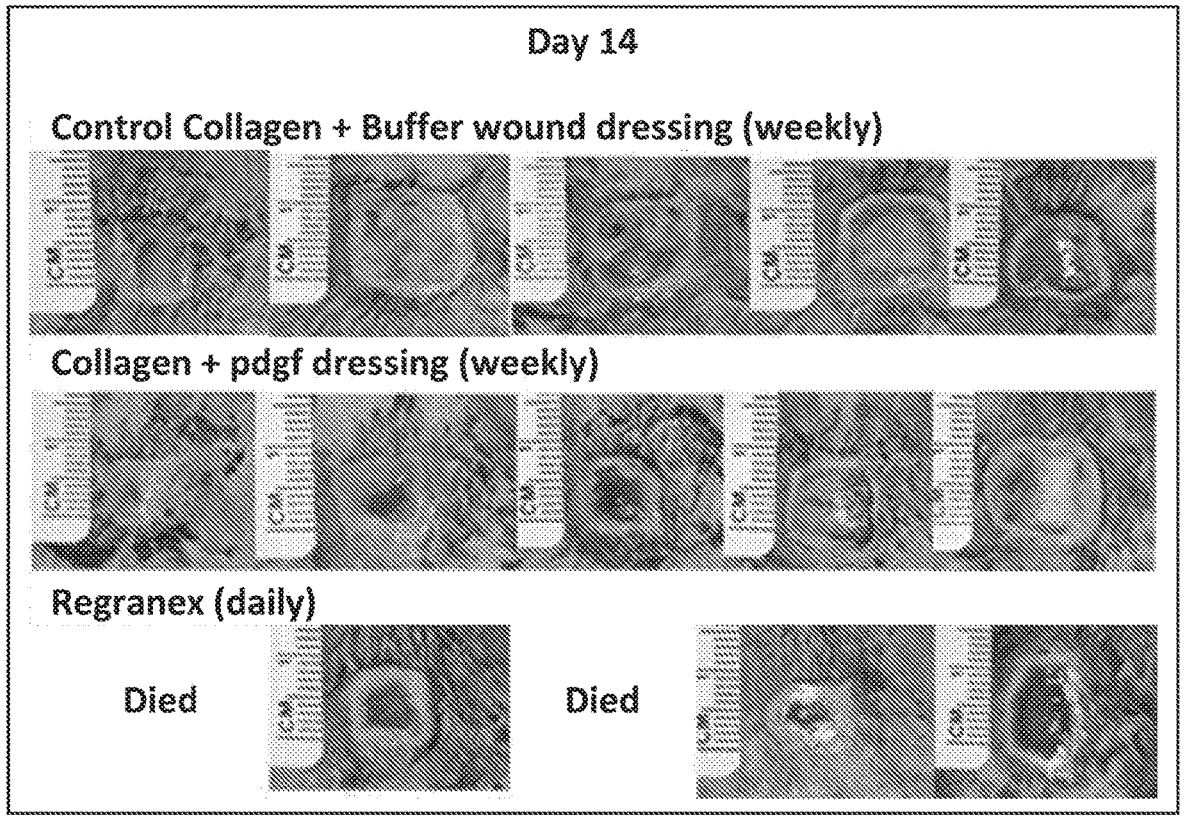

To provide an additional measurement and account for wounds that may not of healed in the shape of a square (and therefore not be captured in the formula used above), the inside of the wounds were also measured by tracing the inside wound edge using ImageJ Software™. FIG. 2 represents the wound area from each animal using this approach for each treatment group. FIGS. 3-6 show the average wound area for all treatment groups by evaluation day (Day 0, Day 7, Day 14, and Day 21) as a scatter plot to provide a more detailed assessment of the individual measurements recorded on those days. For animals that died during the study, the last data point is carried forward in FIGS. 3-6. FIGS. 7A-7B highlights a key aspect of the invention, namely that positive results are achieved with fewer applications of the therapeutic composition. FIG. 7A shows the amount of wound area reduction ($mm^2$) per cumulative number of treatments at each of the four time points (Day 0, Day 7, Day 14, and Day 21) for Groups 1 and 3. FIGS. 8A-8D show the average percent of wound closure over the course of the study for each Group. For animals that died, the last data point was carried forward.

3. Clinical Assessments

Figure 12:
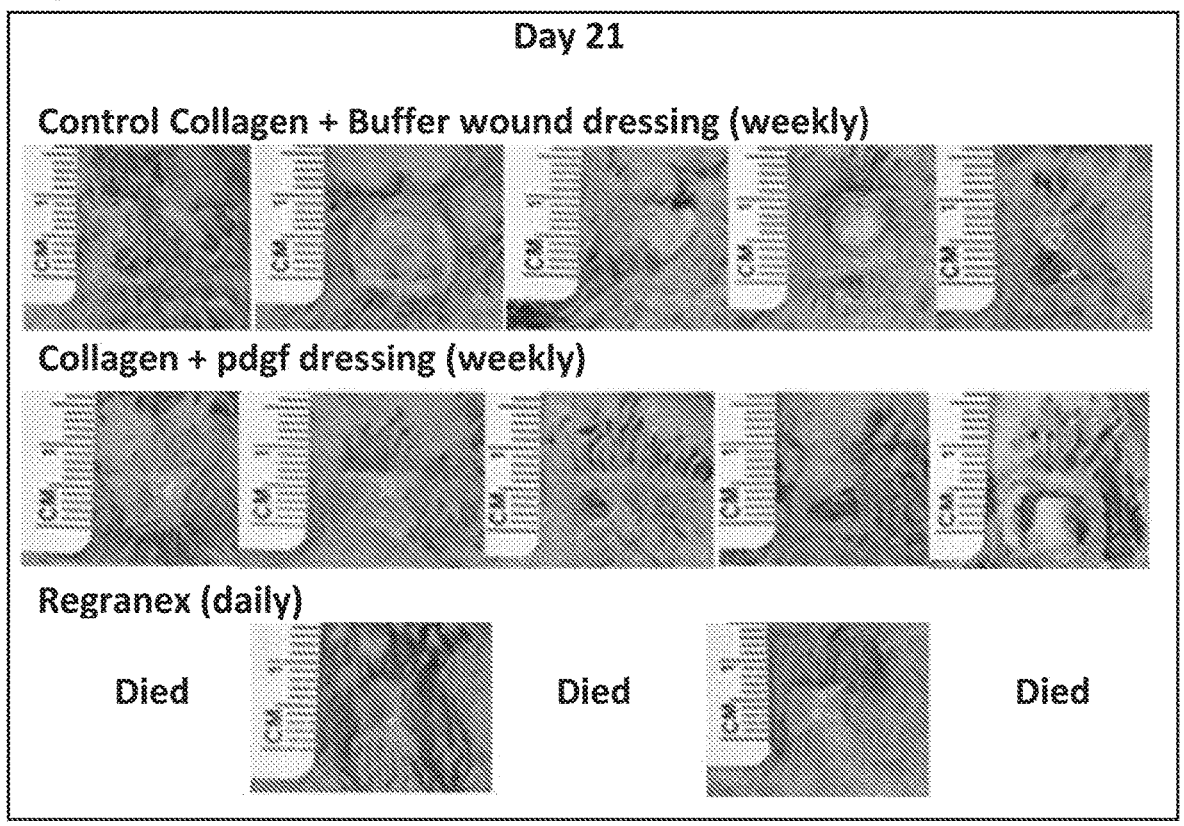

Wound images were also clinically assessed for possible differences in the degree of healing with respect to reepithelialization and formation of granulation tissue. Representative images of the wounds from each animal at each time point are shown in FIGS. 9-12 from Day 0 (FIG. 9), Day 7 (FIG. 10), Day 14 (FIG. 11) and Day 21 (FIG. 12). The raw images from each treatment show that Group 3 (rhPDGF/collagen sponge group) resulted in a demonstrable acceleration in the formation of granulation tissue and re-epithelialization compared to Group 2 (the collagen sponge control group treated with buffer). In addition, wounds treated with Regranex daily (Group 1) also showed a better wound closure rate compared to Group 2 (the buffer control+ collagen). Histopathology on formalin fixed samples of the wound areas was also performed and further corroborated accelerated wound healing resulting from treatment with the rhPDGF/collagen and Regranex treated wounds compared to buffer control treated sponges. The pathology also suggests even further improvement in re-epithelialization in wounds treated with rhPDGF/collagen over Regranex treated.

Figure 13:
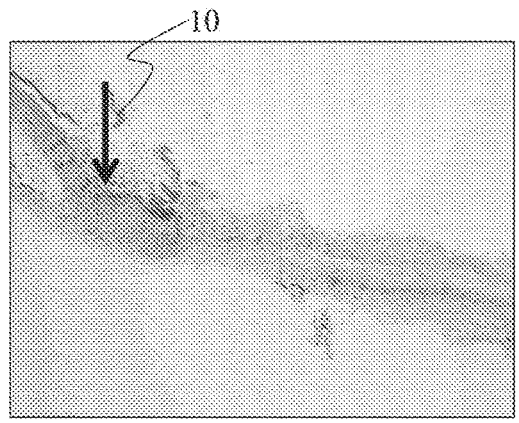
FIGS. 13-18 include a series of photomicrographs of a cross section of the wound site on day 21 from three study animals.
Figure 14:
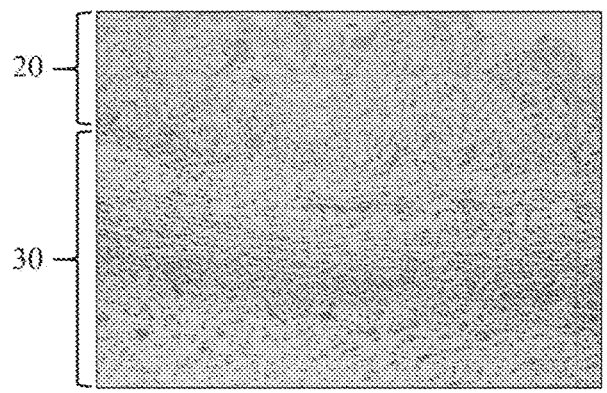
Figure 15:
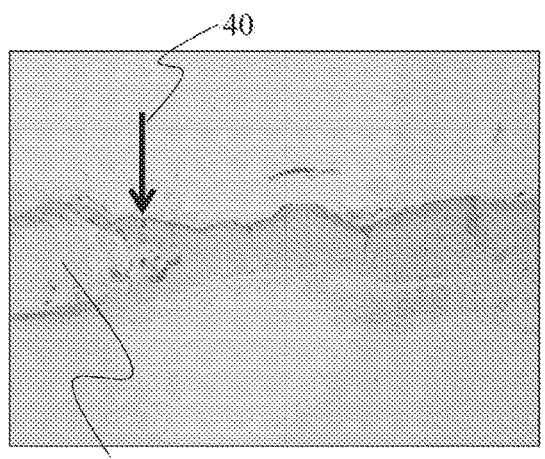
Figure 16:
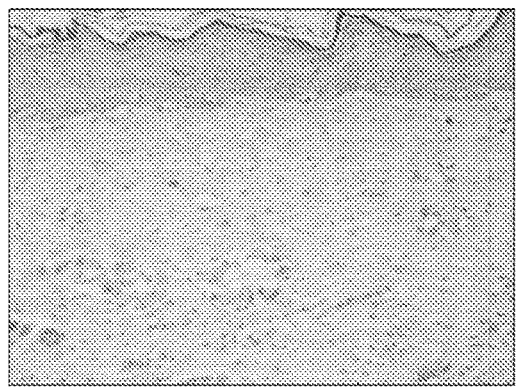
Figure 17:
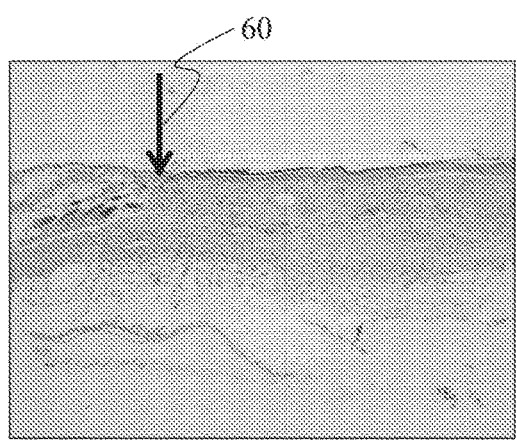
Figure 18:
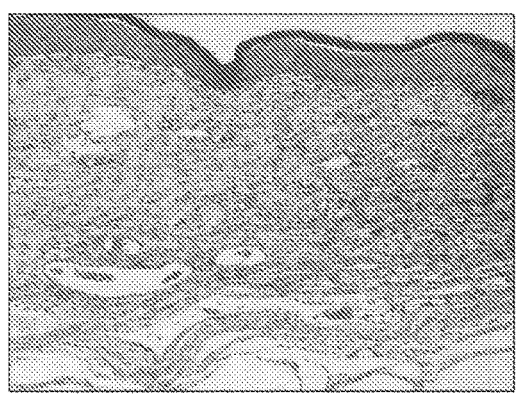

Representative samples of the histopathological samples are provided in FIGS. 13-18 which include a series of photomicrographs of a cross section of the wound site on day 21 from three study animals, including Group 1—Animal 2 (FIGS. 17 and 18), Group 2—Animal 2 (FIGS. 13 and 14), and Group 3—Animal 1 (FIGS. 15 and 16). For each set of photomicrographs there is shown a 2× (FIGS. 13, 15, and 17) and a 10× magnification (FIGS. 14, 16, and 18).

Regarding Group 1, FIGS. 17 and 18 show that the wound was 100% resurfaced at Day 21, although some shearing was apparent due to the fragility of the dermal-epidermal architecture. Arrow 60 in FIG. 17 indicates the approximate location of the adjacent epidermis to the left and the wound bed to the right. FIG. 18 provides a higher magnification image from the middle of the wound. 100% epidermal resurfacing is apparent and the presence of differentiated stratification in the epidermis indicates its maturity. The neodermis still contains a high density of capillaries and new collagen formation is underway.

Regarding Group 2, the photomicrographs illustrate that a portion of the collagen sponge persisted in the wound bed for 21 days. In this wound edge the sponge appeared to obstruct the resurfacing of the epithelium. The arrow 10 in FIG. 13 indicates the wound edge. As seen in FIG. 13, some granulation tissue developed beneath the collagen sponge. Referring to FIG. 14, the collagen sponge and the granulation tissue are indicated by arrows 20 and 30, respectively. As shown, the collagen sponge appeared adherent in this region although infiltration with cells is minimal. A classic granulation tissue is shown formed beneath the sponge.

Regarding Group 3, FIGS. 15 and 16 illustrate the wound is 100% resurfaced with epidermis. The arrow 40 in FIG. 15 indicates the approximate edge of the wound bed, and the region 50 is subcutaneous fat. FIG. 16 was taken within the middle of the wound, and shows that all evidence of the original collagen sponge is gone. The wound is 100% resurfaced and is well stratified with a stratum corneum indicating maturity. The neodermis shows evidence of new collagen production and the cellularity is decreased indicating that the dermal tissue is maturing and losing the immature characteristics of granulation tissue.

E. Study Conclusions

The following conclusions were made from this study:
(1) 21 applications of Regranex were given in Group 1, while only 3 applications of buffer/collagen or rhPDGF/collagen wound dressings were applied in Groups 2 and 3, respectively.
(2) Three animals from Group 1 (Regranex) were either found dead or had to be euthanized during the in-life portion of the study.
(3) All treated groups showed a decrease in wound area from Day 0-21 as determined by both caliper measurements and wound tracing using ImageJ software analysis. At sacrifice (Day 21), 2 of 5 Regranex treated wounds, 3 of 5 rhPDGF/collagen treated wounds and 0 of 5 collagen wound dressing treated wounds were healed.
(4) The raw images from each treatment show that Group 3 (rhPDGF/collagen) results in a demonstrable acceleration in the formation of granulation tissue and re-epithelialization compared to the collagen wound dressing control group treated with buffer (Group 2). In addition, wounds treated with Regranex daily (Group 1) also showed a better closure rate compared to the control collagen sponge treated animals.
(5) Healing as assessed by wound reepithelialization was greatest in wounds treated with three applications of rhPDGF/collagen (Group 3) compared to 21 applications of Regranex (Group 1) or three applications of the collagen wound dressing wetted with saline.
(6) Three (3) weekly applications of rhPDGF/collagen (Group 3) accelerate wound closure, including granulation tissue formation and re-epithelialization compared to a collagen wound dressing (Group 2) and appear at least as effective as 21 daily doses of Regranex Gel (Group 1).
(7) rhPDGF/collagen is safe and effective, promoting better healing of diabetic wounds compared to the marketed collagen wound dressing. 3 of 5 rhPDGF/collagen treated wounds completely healed, as evidenced by complete re-epithelialization, compared to 0 of 5 collagen wound dressing treated animals.
(8) rhPDGF/collagen is safe and effective, promoting angiogenesis, granulation tissue formation and re-epithelialization compared to a marketed collagen wound dressing as demonstrated histologically.
(9) rhPDGF/collagen, a sterile product, is highly biocompatible as demonstrated histologically.
(10) rhPDGF/collagen is much easier to apply than Regranex Gel, which should improve patient compliance.
(11) rhPDGF/collagen may be safer than Regranex, given that animals that received Regranex had a high mortality rate, while no such mortality was observed with rhPDGF/collagen or the collagen wound dressing.

Example 2—Prophetic

A study is conducted to demonstrate the efficacy of the novel therapeutic compositions and wound treatment methods described herein. The same study design outlined for Example 1 is also used for this study including the db/db mouse model with five test groups—a standard of care group (saline moistened gauze), a Regranex group, a collagen sponge group, and two groups utilizing treatment compositions in accordance with the present invention comprising PDGF-BB and a collagen sponge. As detailed below, however, the frequency of the dosing is changed in this study. The study is also designed so that the total dose of PDGF delivered over the course of the study in both the Regranex group and the collagen sponge/PDGF-BB groups is the same.

A. Experimental Design

The experimental design is refined by the results of the study described in Example 1, however it is anticipated that the number of animals per group are greater (i.e. eight) and the study duration is longer, i.e. 28 days. Additionally the test and control collagen +/−PDGF articles are administered topically as wound dressings immediately following the induction of the wound and at about Day 14 for a total of two applications (Group 5) or immediately after surgery and at Days 7, 14 and 21 for a total of four applications of test articles in accordance with the novel compositions and treatment methods described herein (see Table X). Negative control (saline moistened gauze) and Regranex treated sites will undergo 28 daily administrations topically as wound dressing in accordance with the prescribed Instructions for Use.

In this Example, blood glucose levels are determined prior to the start of the study and again just prior to sacrifice on Day 28 to confirm diabetic disease state. In all other aspects, the design for this study is the same as described in Example 1. The study details are outlined in below in Table 3.

TABLE 3

Example 2 Study Design

| Group Number | Number of Animals | Wound | Treatment | Route/Frequency | Dressing Changes & Wound Assessment |
|---|---|---|---|---|---|
| 1 | 8 male (db/db) | Day 0 1.5 cm × 1.5 cm | Saline Moistened Gauze | Topical/28 Daily applications | 27; Daily To Day 28 |
| 2 | 8 male (db/db) | Day 0 1.5 cm × 1.5 cm | Regranex Gel | Topical/28 Daily applications | 27; Daily To Day 28 |
| 3 | 8 male (db/db) | Day 0 1.5 cm × 1.5 cm | Collagen Sponge | Topical/4 applications Days 0, 7, 14 and 21 | 3; Days 7, 14 21 and 28* |
| 4 | 8 male (db/db) | Day 0 1.5 cm × 1.5 cm | Collagen Sponge + 326 µl 0.3 mg/ml PDGF-BB | Topical/4 applications Days 0, 7, 14 and 21 | 3; Days 7, 14, 21 and 28* |
| 5 | 8 male (db/db) | Day 0 1.5 cm × 1.5 cm | Collagen Sponge + 654 µl 0.3 mg/ml PDGF-BB | Topical/2 applications Days 0 and 14 | 1; Day 14, 21# and 28* |

*Wound assessment and necropsy;
Wound assessment only.

Every day for the period of the study, each animal is inspected and its survival recorded, in order to assess possible visual differences in animal responses among treatment groups. The rate of wound closure will be determined, as will the percentage of wounds completely healed at any given time point.

B. PDGF-BB Dose Calculations

The PDGF dosage used in this study is designed to mimic the actual therapeutic doses in accordance with either the present invention (Groups 4 and 5) or the actual therapeutic dose prescribed in accordance with the Regranex label (Group 2). The dosage for Group 2 is determined in the same manner as the Regranex group in Example 1. For sites treated with Regranex for 28 days the total dose of PDGF administered for the study period is 14 µg/day×28 days or 392 µg of PDGF-BB. This dose may also be expressed amount of PDGF per area of the original wound size ("area dose") of 6.22 µg/cm$^2$/day or 174.2 µg/cm$^2$ of PDGF-BB.

For Groups 4 and 5, a PDGF solution is used having a PDGF concentration of 0.3 mg/ml or 300 µg/ml. To achieve a total dose for the study period of 392 µg PDGF-BB (the same total study dose as in the Regranex group), a total of 1.307 ml PDGF solution is applied to the wound site over the 28 day study period. For sites receiving dressing changes once every 7 days there are a total of 4 administrations (days 0, 7, 14 and 21). Each administration consists of 327p PDGF-BB (or buffer alone) onto the collagen sponge. With respect to dose of PDGF, each administration consists of 0.3 µg/µl×326 µl or 98 ug PDGF-BB (approximately 7× Regranex individual dose). For sites receiving just two doses, at Day 0 and 14 there are a total of 2 administrations. Each administration consists of 654 µl PDGF-BB onto the collagen sponge. Each administration would consist of 0.3 µg/µl×654 µl or 196 ug PDGF-BB (approximately 14× Regranex individual dose). These doses may also be expressed as amount of PDGF per area of the original wound size ("area dose"). With respect to Group 4, the PDGF dose is 43.5 µg/cm$^2$/dose or 174 µg/cm$^2$ of PDGF-BB. With respect to Group 5, the PDGF dose is about 87 µg/cm$^2$/dose or 174 µg/cm$^2$ of PDGF, i.e. the same cumulative dose in all groups but Groups 4 and 5 have many fewer doses.

Example 3—Prophetic

A randomized clinical trial is conducted to assess the effectiveness of various compositions of rhPDGF-BB and collagen as compared to standard of care (consisting of moist wound healing with removal of excess wound exudate, debriding necrotic tissue, off-loading of pressure, saline moistened gauze, antibiotics if needed and wound dressing) and Regranex in the treatment of chronic diabetic foot ulcers. Table 4 below summarizes the study design. For each arm of the study (1-37) the product is applied at the dosage and frequency indicated in Table 4 for up to 20 weeks or until complete wound closure. Regranex is applied in accordance with its approve US labeling. rhPDGF-BB/collagen compositions are applied in accordance with the procedures (steps 1-5) described above in paragraph 50.

The outcome measures for the study are:
Incidence of complete wound closure.
Time to achieve complete wound closure.
Percentage reduction in total ulcer surface area at each visit.
Number of ulcer recurrence observed 12 weeks after wound healing.
Treatment emergent adverse events (up to 52 weeks).
The inclusion criteria for the study include:
Men or women aged 18 years old or older, with type 1 or 2 diabetes mellitus
Patient with a single ulcer on the treated feet
Patient able and willing to provide informed consent
Patient able and willing to comply with protocol visits and procedure
Patient willing to use an off-loading method during the whole duration of the study
Full-thickness plantar, lateral or dorsal ulcer of the extremity (below the malleolus), excluding inter-digits ulcer (web spaces), extending through the epidermis and dermis, but not involving bone, tendons, ligaments or muscles (grade IA as defined by University of Texas Diabetic Wound Classification or Grade 1 according to Wagner classification)
Chronic ulcer of at least six weeks despite appropriate wound care
Ulcer area measured with the formula Length×Width×0.8 following sharp debridement, of 1 to 10 cm$^2$, both inclusive
Well controlled infection or cellulitis (systemic antibiotherapy) before Baseline Visit
Peripheral neuropathy as assessed by Semmes-Weinstein monofilament test or by the bio esthesimeter (vibration perception threshold)
Ankle brachial pressure index >0.60 and <1.3

Women surgically sterile, post-menopausal, or agree to practice adequate contraception and have a negative pregnancy test at screening
Non-nursing
The exclusion criteria for the study include:
Inter digit ulcers
Ulcer of other cause or origin: electrical, chemical or radiation insult, bedsores, vascular ulcer or Charcot deformities ulcers
Charcot foot
Wound originated from amputation bed
Active ulcer infection assessed by clinical examination and radiography if necessary. Presence of necrosis, purulence or sinus tracts that cannot be removed by debridement and controlled by standard wound care
Active osteomyelitis affecting the area of the target ulcer
Poorly controlled diabetes (uncontrolled glycemia HbA1c %>=10%), renal failure (serum creatinine >3.0 mg/dL), poor nutritional status (albumin <3.0 g/dL or total protein <6.5 g/dL)
Known connective tissue or malignant disease
Concomitant treatment with corticosteroids, immunosuppressive agents, radiation therapy, or anticancer chemotherapy
Use of investigational drug/device or growth factor within 30 days
Topical application of any advance wound care on this wound (antiseptics, antibiotics, debriders, enzyme) within 7 days
Vascular reconstruction within 8 weeks
Patients expected to be noncompliant with the protocol (not available for the duration of the trial, treatment or wound care compliance), or felt to be unsuitable by the Investigator for any other reason
A history of severe cerebrovascular events

TABLE 4

Example 4 Study Design

| | | Treatment Frequency | Max Number of Treatments | Initial dose (µg/cm2) | Later doses (µg/cm2) | Dosage Adjust | ratio rhPDGF solution/ Collagen (µl/cm3) |
|---|---|---|---|---|---|---|---|
| 1 | Regranex | daily | 140 | 6.25 | 6.25 | weekly | |
| 2 | Standard of Care | daily | 140 | — | — | — | |
| 3 | rhPDGF/collagen | 3 days | 46 | 10 | 10 | 6 days | 67 |
| 4 | sponge | 3 days | 46 | 18.75 | 18.75 | 6 days | 125 |
| 5 | | 5 days | 28 | 31.25 | 31.25 | 10 days | 208 |
| 6 | | 7 days | 20 | 43.75 | 43.75 | 7 days | 292 |
| 7 | | 14 days | 10 | 87.5 | 87.5 | 14 days | 583 |
| 8 | | 21 days | 6 | 131.25 | 131.25 | 21 days | 875 |
| 9 | | 28 days | 5 | 175 | 175 | 28 days | 1167 |
| 10 | | 35 days | 4 | 218.75 | 218.75 | 35 days | 1459 |
| 11 | | 42 days | 3 | 262.5 | 262.5 | 42 days | 1750 |
| 12 | | 3 days | 46 | 10 | 10 | 6 days | 134 |
| 13 | | 3 days | 46 | 18.75 | 18.75 | 6 days | 250 |
| 14 | | 5 days | 28 | 31.25 | 31.25 | 10 days | 416 |
| 15 | | 7 days | 20 | 43.75 | 43.75 | 7 days | 584 |
| 16 | | 14 days | 10 | 87.5 | 87.5 | 14 days | 1166 |
| 17 | | 21 days | 6 | 131.25 | 131.25 | 21 days | 1750 |
| 18 | | 28 days | 5 | 175 | 175 | 28 days | 2334 |
| 19 | | 35 days | 4 | 218.75 | 218.75 | 35 days | 2918 |
| 20 | | 42 days | 3 | 262.5 | 262.5 | 42 days | 3500 |
| 21 | | 3 days | 46 | 20 | 10 | 6 days | 67 |
| 22 | | 3 days | 46 | 37.5 | 18.75 | 6 days | 125 |
| 23 | | 5 days | 28 | 62.5 | 31.25 | 10 days | 208 |
| 24 | | 7 days | 20 | 87.5 | 43.75 | 7 days | 292 |
| 25 | | 14 days | 10 | 175 | 87.5 | 14 days | 583 |
| 26 | | 21 days | 6 | 262.5 | 131.25 | 21 days | 875 |
| 27 | | 28 days | 5 | 350 | 175 | 28 days | 1167 |
| 28 | | 35 days | 4 | 437.5 | 218.75 | 35 days | 1459 |
| 29 | | 42 days | 3 | 525 | 262.5 | 42 days | 1750 |
| 30 | | 3 days | 46 | 18.75 | 18.75 | 6 days | 250 |
| 31 | | 5 days | 28 | 31.25 | 31.25 | 10 days | 370 |
| 32 | | 7 days | 20 | 43.75 | 43.75 | 7 days | 480 |
| 33 | | 14 days | 10 | 87.5 | 87.5 | 14 days | 890 |
| 34 | | 21 days | 6 | 131.25 | 131.25 | 21 days | 1290 |
| 35 | | 28 days | 5 | 175 | 175 | 28 days | 1690 |
| 36 | | 35 days | 4 | 218.75 | 218.75 | 35 days | 2100 |
| 37 | | 42 days | 3 | 262.5 | 262.5 | 42 days | 2500 |

Each of the rhPDGF/collagen sponge compositions performs better than Regranex or standard of care in at least one of the outcome measures, and/or achieves a substantially equivalent result with the application of less cumulative rhPDGF applied over the treatment period or the application of fewer treatments which leads to better patient compliance.

The embodiments, variations, and sequences described herein should provide an indication of the utility and versatility of the present invention. Other embodiments that do not provide all of the features and advantages set forth herein may also be utilized, without departing from the spirit and scope of the present invention. Such modifications and variations are considered to be within the scope of the invention.

The invention claimed is:

1. A method of treating a wound that extends through the epidermis, wherein said method comprises:
   (1) debriding the wound to remove necrotic or infected tissue;
   (2) forming a therapeutic composition consisting essentially of sterile recombinant human PDGF-BB (rhPDGF-BB) in a physiologic solution and a sterile porous biocompatible carrier, wherein the porous biocompatible carrier is a collagen sponge or collagen wound dressing, and said therapeutic composition is free from an enzyme inhibitor;
   (3) applying the therapeutic composition to the wound surface in an amount that is at least about 10 µg rhPDGF-BB per cm² of treated wound surface area up to about 100 µg rhPDGF-BB per cm² of treated wound surface area, wherein the carrier provides a substrate for cell attachment and vascular ingrowth as the wound heals;
   (4) covering the wound with a dressing; and
   (5) monitoring the healing of the wound during a treatment period and repeating steps (1)-(4) to retreat the wound at treatment intervals of 7 or more days, wherein the wound is retreated from 2 to 20 times, and wherein each retreatment comprises applying the therapeutic composition to the wound surface in an amount that is at least 10 µg rhPDGF-BB/cm² treated wound surface area up to 100 µg rhPDGF-BB/cm² treated wound surface area.

2. The method of claim 1 wherein the wound extends through the epidermis for at least six weeks duration.

3. The method of claim 1 wherein the wound is an ulcer.

4. The method of claim 1 wherein the wound is a diabetic foot ulcer.

5. The method of claim 1 wherein the wound is a venous stasis ulcer.

6. The method of claim 1 wherein the wound is a pressure ulcer.

7. The method of claim 1 wherein the wound is an accidental acute wound or surgical wound.

8. The method of claim 1 wherein the step of forming the therapeutic composition comprises combining the sterile rhPDGF-BB and the sterile porous biocompatible carrier, wherein:
   (i) the sterile rhPDGF-BB comprises an rhPDGF-BB solution comprising between about 0.05 mg/ml to about 5 mg/ml of rhPDGF-BB, and
   (ii) the ratio of the rhPDGF-BB solution to the carrier is between about 0.1 ml solution/cm³ of carrier to about 1 ml solution/cm³ of carrier, or the ratio of rhPDGF-BB to the carrier is between about 75 µg rhPDGF-BB/cm³ of carrier to about 225 µg rhPDGF-BB/cm³ of carrier.

9. The method of claim 1 wherein the step of forming the therapeutic composition comprises combining the sterile rhPDGF-BB and the sterile porous biocompatible carrier, wherein:
   (i) the sterile rhPDGF-BB comprises an rhPDGF-BB solution comprising between about 0.05 mg/ml to about 5 mg/ml of rhPDGF-BB, and
   (ii) the ratio of the rhPDGF-BB solution to the carrier is between about 0.25 ml solution/cm³ of carrier to about 5 ml solution/cm³ of carrier, or the ratio of rhPDGF-BB to the carrier is between about 75 µg rhPDGF-BB/cm³ of carrier to about 750 µg rhPDGF-BB/cm³ of carrier.

10. The method of claim 1 wherein when the rhPDGF-BB and the porous biocompatible carrier are combined, the carrier is capable of entrapping the rhPDGF-BB within its pores such that the rhPDGF-BB is released over time as the carrier is absorbed by the patient's body, thereby providing controlled delivery of rhPDGF-BB at the wound over an extended period of time and simultaneously providing a matrix for new cell and tissue ingrowth.

11. The method of claim 1 wherein at least about 80% of the rhPDGF-BB on a weight basis is unclipped rhPDGF-BB.

12. The method of claim 1 wherein the porous biocompatible carrier is a collagen sponge.

13. The method of claim 1 wherein the porous biocompatible carrier is a collagen wound dressing.

14. The method of claim 1 wherein the cumulative total amount of rhPDGF-BB applied to the wound during the treatment period is less than about 50 mg of rhPDGF-BB.

15. The method of claim 1 wherein the cumulative total amount of rhPDGF-BB applied to the wound during the treatment period is less than about 25 mg of rhPDGF-BB.

16. The method of claim 1 wherein the wound is retreated from 2 to 20 times over a maximum treatment period of 2 to 20 weeks.

17. The method of claim 1 wherein the steps (1)-(4) are repeated to retreat the wound at a retreatment frequency of at least every 8 days.

18. The method of claim 1 wherein the steps (1)-(4) are repeated to retreat the wound at a retreatment frequency of at least every 10 days.

19. The method of claim 1 wherein the wound is retreated a maximum of 10 times.

20. The method of claim 1 wherein:
(A) the wound extends through the epidermis for at least six weeks duration;
(B) the step of forming the therapeutic composition comprises combining the sterile rhPDGF-BB and the sterile porous biocompatible carrier, wherein:
  (i) the sterile rhPDGF-BB comprises an rhPDGF-BB solution comprising between about 0.05 mg/ml to about 5 mg/ml of rhPDGF-BB, wherein at least about 80% of the rhPDGF-BB on a weight basis is unclipped rhPDGF-BB, and
  (ii) the ratio of the rhPDGF-BB solution to the carrier is between about 0.1 ml solution/cm$^3$ of carrier to about 1 ml solution/cm$^3$ of carrier, or the ratio of rhPDGF-BB to the carrier is between about 75 μg rhPDGF-BB/cm$^3$ of carrier to about 225 μg rhPDGF-BB/cm$^3$ of carrier;
(C) the wound is retreated from 2 to 20 times over a maximum treatment period of 2 to 20 weeks at a retreatment frequency of at least every 8 days; and
(D) the cumulative total amount of rhPDGF-BB applied to the wound during the treatment period is less than about 50 mg of rhPDGF-BB.

21. A method of treating a wound that extends through the epidermis, wherein said method comprises:
(1) debriding the wound to remove necrotic or infected tissue;
(2) forming a therapeutic composition consisting essentially of sterile recombinant human PDGF-BB (rhPDGF-BB) in a physiologic solution and a sterile porous biocompatible carrier, wherein the porous biocompatible carrier is a collagen sponge or collagen wound dressing;
(3) applying the therapeutic composition to the wound surface in an amount that is at least about 10 μg rhPDGF-BB per cm$^2$ of treated wound surface area up to about 100 μg rhPDGF-BB per cm$^2$ of treated wound surface area, wherein the carrier provides a substrate for cell attachment and vascular ingrowth as the wound heals;
(4) covering the wound with a dressing; and
(5) monitoring the healing of the wound during a treatment period and repeating steps (1)-(4) to retreat the wound at treatment intervals of 8 or more days, wherein the wound is retreated from 2 to 20 times over a maximum treatment period of 2 to 20 weeks, and wherein each retreatment comprises applying the therapeutic composition to the wound surface in an amount that is at least 10 μg rhPDGF-BB/cm$^2$ treated wound surface area up to 100 μg rhPDGF-BB/cm$^2$ treated wound surface area.

22. The method of claim 21 wherein the wound is a wound that extends through the dermis for at least six weeks duration.

23. The method of claim 21 wherein the wound is an ulcer.

24. The method of claim 21 wherein the wound is a diabetic foot ulcer.

25. The method of claim 21 wherein the wound is a venous stasis ulcer.

26. The method of claim 21 wherein the wound is a pressure ulcer.

27. The method of claim 21 wherein the wound is an accidental acute wound or surgical wound.

28. The method of claim 21 wherein the step of forming the therapeutic composition comprises combining the sterile rhPDGF-BB and the sterile porous biocompatible carrier, wherein:
  (i) the sterile rhPDGF-BB comprises an rhPDGF-BB solution comprising between about 0.05 mg/ml to about 5 mg/ml of rhPDGF-BB, and
  (ii) the ratio of the rhPDGF-BB solution to the carrier is between about 0.1 ml solution/cm$^3$ of carrier to about 1 ml solution/cm$^3$ of carrier, or the ratio of rhPDGF-BB to the carrier is between about 75 μg rhPDGF-BB/cm$^3$ of carrier to about 225 μg rhPDGF-BB/cm$^3$ of carrier.

29. The method of claim 21 wherein the step of forming the therapeutic composition comprises combining the sterile rhPDGF-BB and the sterile porous biocompatible carrier, wherein:
  (i) the sterile rhPDGF-BB comprises an rhPDGF-BB solution comprising between about 0.05 mg/ml to about 5 mg/ml of rhPDGF-BB, and
  (ii) the ratio of the rhPDGF-BB solution to the carrier is between about 0.25 ml solution/cm$^3$ of carrier to about 5 ml solution/cm$^3$ of carrier, or the ratio of rhPDGF-BB to the carrier is between about 75 μg rhPDGF-BB/cm$^3$ of carrier to about 750 μg rhPDGF-BB/cm$^3$ of carrier.

30. The method of claim 21 wherein the cumulative total amount of rhPDGF-BB applied to the wound during the treatment period is less than about 50 mg of rhPDGF-BB.

31. The method of claim 21 wherein the cumulative total amount of rhPDGF-BB applied to the wound during the treatment period is less than about 25 mg of rhPDGF-BB.

32. The method of claim 21 wherein the steps (1)-(4) are repeated to retreat the wound at a retreatment frequency of at least every 10 days.

33. The method of claim 21 wherein the wound is retreated a maximum of 10 times.

34. The method of claim 21 wherein:
(A) the wound extends through the epidermis for at least six weeks duration;
(B) the step of forming the therapeutic composition comprises combining the sterile rhPDGF-BB and the sterile porous biocompatible carrier, wherein:
  (i) the sterile rhPDGF-BB comprises an rhPDGF-BB solution comprising between about 0.05 mg/ml to about 5 mg/ml of rhPDGF-BB, wherein at least about 80% of the rhPDGF-BB on a weight basis is unclipped rhPDGF-BB, and (ii) the ratio of the rhPDGF-BB solution to the carrier is between about 0.1 ml solution/cm$^3$ of carrier to about 1 ml solution/cm$^3$ of carrier, or the ratio of rhPDGF-BB to the carrier is between about 75 μg rhPDGF-BB/cm$^3$ of carrier to about 225 μg rhPDGF-BB/cm$^3$ of carrier; and (C) the cumulative total amount of rhPDGF-BB applied to the wound during the treatment period is less than about 50 mg of rhPDGF-BB.

35. A method of treating a wound that extends through the epidermis, wherein said method comprises:
   (1) debriding the wound to remove necrotic or infected tissue;
   (2) forming a therapeutic composition consisting essentially of sterile recombinant human PDGF-BB (rhPDGF-BB) in a physiologic solution and a sterile porous biocompatible carrier, wherein the porous biocompatible carrier is a collagen sponge or collagen wound dressing;
   (3) applying the therapeutic composition to the wound surface in an amount that is at least about 10 μg rhPDGF-BB per cm$^2$ of treated wound surface area up to about 100 μg rhPDGF-BB per cm$^2$ of treated wound surface area, wherein the carrier provides a substrate for cell attachment and vascular ingrowth as the wound heals;
   (4) covering the wound with a dressing; and
   (5) monitoring the healing of the wound during a treatment period and repeating steps (1)-(4) to retreat the wound at treatment intervals of 10 or more days,
   wherein the wound is retreated from 2 to 20 times, and wherein each retreatment comprises applying the therapeutic composition to the wound surface in an amount that is at least 10 μg rhPDGF-BB/cm$^2$ treated wound surface area up to 100 μg rhPDGF-BB/cm$^2$ treated wound surface area.

36. The method of claim 35 wherein the wound extends through the epidermis for at least six weeks duration.

37. The method of claim 35 wherein the wound is an ulcer.

38. The method of claim 35 wherein the wound is a diabetic foot ulcer.

39. The method of claim 35 wherein the wound is a venous stasis ulcer.

40. The method of claim 35 wherein the wound is a pressure ulcer.

41. The method of claim 35 wherein the wound is an accidental acute wound or surgical wound.

42. The method of claim 35 wherein the step of forming the therapeutic composition comprises combining the sterile rhPDGF-BB and the sterile porous biocompatible carrier, wherein:
   (i) the sterile rhPDGF-BB comprises an rhPDGF-BB solution comprising between about 0.05 mg/ml to about 5 mg/ml of rhPDGF-BB, and
   (ii) the ratio of the rhPDGF-BB solution to the carrier is between about 0.1 ml solution/cm$^3$ of carrier to about 1 ml solution/cm$^3$ of carrier, or the ratio of rhPDGF-BB to the carrier is between about 75 μg rhPDGF-BB/cm$^3$ of carrier to about 225 μg rhPDGF-BB/cm$^3$ of carrier.

43. The method of claim 35 wherein the step of forming the therapeutic composition comprises combining the sterile rhPDGF-BB and the sterile porous biocompatible carrier, wherein:
   (i) the sterile rhPDGF-BB comprises an rhPDGF-BB solution comprising between about 0.05 mg/ml to about 5 mg/ml of rhPDGF-BB, and
   (ii) the ratio of the rhPDGF-BB solution to the carrier is between about 0.25 ml solution/cm$^3$ of carrier to about 5 ml solution/cm$^3$ of carrier, or the ratio of rhPDGF-BB to the carrier is between about 75 μg rhPDGF-BB/cm$^3$ of carrier to about 750 μg rhPDGF-BB/cm$^3$ of carrier.

44. The method of claim 35 wherein the cumulative total amount of rhPDGF-BB applied to the wound during the treatment period is less than about 50 mg of rhPDGF-BB.

45. The method of claim 35 wherein the cumulative total amount of rhPDGF-BB applied to the wound during the treatment period is less than about 25 mg of rhPDGF-BB.

46. The method of claim 35 wherein the wound is retreated from 2 to 22 times over a maximum treatment period of 2 to 20 weeks.

47. A method of treating a wound that is a burn extending through the epidermis, wherein said method comprises:
   (1) debriding the wound to remove necrotic or infected tissue;
   (2) forming a therapeutic composition consisting essentially of sterile recombinant human PDGF-BB (rhPDGF-BB) in a physiologic solution and a sterile porous biocompatible carrier, wherein the porous biocompatible carrier is a collagen sponge or collagen wound dressing, and said therapeutic composition is free from an enzyme inhibitor;
   (3) applying the therapeutic composition to the wound surface in an amount that is at least about 1014 rhPDGF-BB per cm$^2$ of treated wound surface area up to about 10014 rhPDGF-BB per cm$^2$ of treated wound surface area, wherein the carrier provides a substrate for cell attachment and vascular ingrowth as the wound heals;
   (4) covering the wound with a dressing; and
   (5) monitoring the healing of the wound during a treatment period and repeating steps (1)-(4) to retreat the wound at treatment intervals of 7 or more days,
   wherein the wound is retreated from 2 to 20 times, and wherein each retreatment comprises applying the therapeutic composition to the wound surface in an amount that is at least 10 μg rhPDGF-BB/cm$^2$ treated wound surface area up to 100 μg rhPDGF-BB/cm$^2$ treated wound surface area.

48. The method of claim 47 wherein the step of forming the therapeutic composition comprises combining the sterile rhPDGF-BB and the sterile porous biocompatible carrier, wherein:
   (i) the sterile rhPDGF-BB comprises an rhPDGF-BB solution comprising between about 0.05 mg/ml to about 5 mg/ml of rhPDGF-BB, and
   (ii) the ratio of the rhPDGF-BB solution to the carrier is between about 0.1 ml/cm$^3$ carrier to about 1 ml/cm$^3$, or the ratio of rhPDGF-BB to the carrier is between about 75 μg rhPDGF-BB/cm$^3$ of carrier to about 225 μg rhPDGF-BB/cm$^3$ of carrier.

49. The method of claim 47 wherein the step of forming the therapeutic composition comprises combining the sterile rhPDGF-BB and the sterile porous biocompatible carrier, wherein:
   (i) the sterile rhPDGF-BB comprises an rhPDGF-BB solution comprising between about 0.05 mg/ml to about 5 mg/ml of rhPDGF-BB, and
   (ii) the ratio of the rhPDGF-BB solution to the carrier is between about 0.25 ml solution/cm$^3$ of carrier to about 5 ml solution/cm$^3$ of carrier, or the ratio of rhPDGF-BB to the carrier is between about 75 μg rhPDGF-BB/cm$^3$ of carrier to about 750 μg rhPDGF-BB/cm$^3$ of carrier.

50. The method of claim 47 wherein when the rhPDGF-BB and the porous biocompatible carrier are combined, the carrier is capable of entrapping the rhPDGF-BB within its pores such that the rhPDGF-BB is released over time as the carrier is absorbed by the patient's body, thereby providing controlled delivery of rhPDGF-BB at the wound over an extended period of time and simultaneously providing a matrix for new cell and tissue ingrowth.

51. The method of claim 47 wherein at least about 80% of the rhPDGF-BB on a weight basis is unclipped rhPDGF-BB.

52. The method of claim 47 wherein the porous biocompatible carrier is a collagen sponge.

53. The method of claim 47 wherein the porous biocompatible carrier is a collagen wound dressing.

54. The method of claim 47 wherein the cumulative total amount of rhPDGF-BB applied to the wound during the treatment period is less than about 50 mg of rhPDGF-BB.

55. The method of claim 47 wherein the cumulative total amount of rhPDGF-BB applied to the wound during the treatment period is less than about 25 mg of rhPDGF-BB.

56. The method of claim 47 wherein the wound is retreated from 2 to 22 times over a maximum treatment period of 2 to 20 weeks.

57. The method of claim 47 wherein the steps (1)-(4) are repeated to retreat the wound at a retreatment frequency of at least every 8 days.

58. The method of claim 47 wherein the steps (1)-(4) are repeated to retreat the wound at a retreatment frequency of at least every 10 days.

59. The method of claim 47 wherein the wound is retreated a maximum of 10 times.

60. The method of claim 47 wherein:
(A) the wound is a burn of a least six weeks duration;
(B) the step of forming the therapeutic composition comprises combining the sterile rhPDGF-BB and the sterile porous biocompatible carrier, wherein:
    (i) the sterile rhPDGF-BB comprises an rhPDGF-BB solution comprising between about 0.05 mg/ml to about 5 mg/ml of rhPDGF-BB, wherein at least about 80% of the rhPDGF-BB on a weight basis is unclipped rhPDGF-BB, and
    (ii) the ratio of the rhPDGF-BB solution to the carrier is between about 0.1 ml solution/cm$^3$ of carrier to about 1 ml solution/cm$^3$ of carrier, or the ratio of rhPDGF-BB to the carrier is between about 75 μg rhPDGF-BB/cm$^3$ of carrier to about 225 μg rhPDGF-BB/cm$^3$ of carrier;
(C) the wound is retreated from 2 to 20 times over a maximum treatment period of 2 to 20 weeks at a retreatment frequency of at least every 8 days; and
(D) the cumulative total amount of rhPDGF-BB applied to the wound during the treatment period is less than about 50 mg of rhPDGF-BB.

61. A method of treating a wound that is a burn extending through the epidermis, wherein said method comprises:
(1) debriding the wound to remove necrotic or infected tissue;
(2) forming a therapeutic composition consisting essentially of sterile recombinant human PDGF-BB (rhPDGF-BB) in a physiologic solution and a sterile porous biocompatible carrier, wherein the porous biocompatible carrier is a collagen sponge or collagen wound dressing;
(3) applying the therapeutic composition to the wound surface in an amount that is at least about 10 μg rhPDGF-BB per cm$^2$ of treated wound surface area up to about 100 μg rhPDGF-BB per cm$^2$ of treated wound surface area, wherein the carrier provides a substrate for cell attachment and vascular ingrowth as the wound heals;
(4) covering the wound with a dressing; and
(5) monitoring the healing of the wound during a treatment period and repeating steps (1)-(4) to retreat the wound at treatment intervals of 8 or more days,
wherein the wound is retreated from 2 to 20 times over a maximum treatment period of 2 to 20 weeks, and wherein each retreatment comprises applying the therapeutic composition to the wound surface in an amount that is at least 10 μg rhPDGF-BB/cm$^2$ treated wound surface area up to 100 μg rhPDGF-BB/cm$^2$ treated wound surface area.

62. The method of claim 61 wherein the step of forming the therapeutic composition comprises combining the sterile rhPDGF-BB and the sterile porous biocompatible carrier, wherein:
(i) the sterile rhPDGF-BB comprises an rhPDGF-BB solution comprising between about 0.05 mg/ml to about 5 mg/ml of rhPDGF-BB, and
(ii) the ratio of the rhPDGF-BB solution to the carrier is between about 0.1 ml solution/cm$^3$ of carrier to about 1 ml solution/cm$^3$ of carrier, or the ratio of rhPDGF-BB to the carrier is between about 75 μg rhPDGF-BB/cm$^3$ of carrier to about 225 μg rhPDGF-BB/cm$^3$ of carrier.

63. The method of claim 61 wherein the step of forming the therapeutic composition comprises combining the sterile rhPDGF-BB and the sterile porous biocompatible carrier, wherein:
(i) the sterile rhPDGF-BB comprises an rhPDGF-BB solution comprising between about 0.05 mg/ml to about 5 mg/ml of rhPDGF-BB, and
(ii) the ratio of the rhPDGF-BB solution to the carrier is between about 0.25 ml solution/cm$^3$ of carrier to about 5 ml solution/cm$^3$ of carrier, or the ratio of rhPDGF-BB to the carrier is between about 75 μg rhPDGF-BB/cm$^3$ of carrier to about 750 μg rhPDGF-BB/cm$^3$ of carrier.

64. The method of claim 61 wherein the cumulative total amount of rhPDGF-BB applied to the wound during the treatment period is less than about 50 mg of rhPDGF-BB.

65. The method of claim 61 wherein the cumulative total amount of rhPDGF-BB applied to the wound during the treatment period is less than about 25 mg of rhPDGF-BB.

66. The method of claim 61 wherein the steps (1)-(4) are repeated to retreat the wound at a retreatment frequency of at least every 10 days.

67. The method of claim 61 wherein the wound is retreated a maximum of 10 times.

68. The method of claim 61 wherein:
(A) the wound is a burn of at least six weeks duration;
(B) the step of forming the therapeutic composition comprises combining the sterile rhPDGF-BB and the sterile porous biocompatible carrier, wherein:
    (i) the sterile rhPDGF-BB comprises an rhPDGF-BB solution comprising between about 0.05 mg/ml to about 5 mg/ml of rhPDGF-BB, wherein at least about 80% of the rhPDGF-BB on a weight basis is unclipped rhPDGF-BB, and
    (ii) the ratio of the rhPDGF-BB solution to the carrier is between about 0.1 ml solution/cm$^3$ of carrier to about 1 ml solution/cm$^3$ of carrier, or the ratio of rhPDGF-BB to the carrier is between about 75 μg rhPDGF-BB/cm$^3$ of carrier to about 225 μg rhPDGF-BB/cm$^3$ of carrier; and (C) the cumulative total amount of rhPDGF-BB applied to the wound during the treatment period is less than about 50 mg of rhPDGF-BB.

69. A method of treating a wound that is a burn extending through the epidermis, wherein said method comprises:
  (1) debriding the wound to remove necrotic or infected tissue;
  (2) forming a therapeutic composition consisting essentially of sterile recombinant human PDGF-BB (rhPDGF-BB) in a physiologic solution and a sterile porous biocompatible carrier, wherein the porous biocompatible carrier is a collagen sponge or collagen wound dressing;
  (3) applying the therapeutic composition to the wound surface in an amount that is at least about 10 µg rhPDGF-BB per cm² of treated wound surface area up to about 100 µg rhPDGF-BB per cm² of treated wound surface area, wherein the carrier provides a substrate for cell attachment and vascular ingrowth as the wound heals;
  (4) covering the wound with a dressing; and
  (5) monitoring the healing of the wound during a treatment period and repeating steps (1)-(4) to retreat the wound at treatment intervals of 10 or more days,
  wherein the wound is retreated from 2 to 20 times, and wherein each retreatment comprises applying the therapeutic composition to the wound surface in an amount that is at least 10 µg rhPDGF-BB/cm² treated wound surface area up to 100 µg rhPDGF-BB/cm² treated wound surface area.

70. The method of claim 69 wherein the step of forming the therapeutic composition comprises combining the sterile rhPDGF-BB and the sterile porous biocompatible carrier, wherein:
  (i) the sterile rhPDGF-BB comprises an rhPDGF-BB solution comprising between about 0.05 mg/ml to about 5 mg/ml of rhPDGF-BB, and
  (ii) the ratio of the rhPDGF-BB solution to the carrier is between about 0.1 ml solution/cm³ of carrier to about 1 ml solution/cm³ of carrier, or the ratio of rhPDGF-BB to the carrier is between about 75 µg rhPDGF-BB/cm³ of carrier to about 225 µg rhPDGF-BB/cm³ of carrier.

71. The method of claim 69 wherein the step of forming the therapeutic composition comprises combining the sterile rhPDGF-BB and the sterile porous biocompatible carrier, wherein:
  (i) the sterile rhPDGF-BB comprises an rhPDGF-BB solution comprising between about 0.05 mg/ml to about 5 mg/ml of rhPDGF-BB, and
  (ii) the ratio of the rhPDGF-BB solution to the carrier is between about 0.25 ml solution/cm³ of carrier to about 5 ml solution/cm³ of carrier, or the ratio of rhPDGF-BB to the carrier is between about 75 µg rhPDGF-BB/cm³ of carrier to about 750 µg rhPDGF-BB/cm³ of carrier.

72. The method of claim 69 wherein the cumulative total amount of rhPDGF-BB applied to the wound during the treatment period is less than about 50 mg of rhPDGF-BB.

73. The method of claim 69 wherein the cumulative total amount of rhPDGF-BB applied to the wound during the treatment period is less than about 25 mg of rhPDGF-BB.

74. The method of claim 69 wherein the wound is retreated from 2 to 22 times over a maximum treatment period of 2 to 20 weeks.

* * * * *

SEQUENCE LISTING

<160> NUMBER OF SEQ ID NOS: 1

<210> SEQ ID NO 1
<211> LENGTH: 109
<212> TYPE: PRT
<213> ORGANISM: Artificial Sequence
<220> FEATURE:
<223> OTHER INFORMATION: Synthetic Construct

<400> SEQUENCE: 1

```
Ser Leu Gly Ser Leu Thr Ile Ala Glu Pro Ala Met Ile Ala Glu Cys
 1               5                  10                  15

Lys Thr Arg Thr Glu Val Phe Glu Ile Ser Arg Arg Leu Ile Asp Arg
            20                  25                  30

Thr Asn Ala Asn Phe Leu Val Trp Pro Pro Cys Val Glu Val Gln Arg
        35                  40                  45

Cys Ser Gly Cys Cys Asn Asn Arg Asn Val Gln Cys Arg Pro Thr Gln
    50                  55                  60

Val Gln Leu Arg Pro Val Gln Val Arg Lys Ile Glu Ile Val Arg Lys
65                  70                  75                  80

Lys Pro Ile Phe Lys Lys Ala Thr Val Thr Leu Glu Asp His Leu Ala
                85                  90                  95

Cys Lys Cys Glu Thr Val Ala Ala Ala Arg Pro Val Thr
            100                 105
```